United States Patent
Holub et al.

(10) Patent No.: US 11,298,176 B2
(45) Date of Patent: Apr. 12, 2022

(54) SURGICAL DEVICE MULTI-SOCKET, ELECTRO-SURGICAL HIGH-FREQUENCY GENERATOR, ELECTRO-SURGICAL DEVICE PLUG AND ELECTRO-SURGICAL SYSTEM

(71) Applicant: OLYMPUS WINTER & IBE GMBH, Hamburg (DE)

(72) Inventors: Benjamin Holub, Berlin (DE); Mario Arnold, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 804 days.

(21) Appl. No.: 16/066,885

(22) PCT Filed: Feb. 15, 2017

(86) PCT No.: PCT/EP2017/053400
§ 371 (c)(1),
(2) Date: Jun. 28, 2018

(87) PCT Pub. No.: WO2017/140727
PCT Pub. Date: Aug. 24, 2017

(65) Prior Publication Data
US 2019/0008575 A1 Jan. 10, 2019

(30) Foreign Application Priority Data
Feb. 15, 2016 (DE) ................ 10 2016 102 640.9

(51) Int. Cl.
*H01R 9/05* (2006.01)
*A61B 18/12* (2006.01)
(Continued)

(52) U.S. Cl.
CPC .......... *A61B 18/1206* (2013.01); *H01R 9/05* (2013.01); *H01R 27/02* (2013.01);
(Continued)

(58) Field of Classification Search
CPC . H01R 9/05; H01R 9/02; H01R 27/02; H01R 24/40; H01R 2201/12; A61B 2018/00178; A61B 2018/1253
(Continued)

(56) References Cited

U.S. PATENT DOCUMENTS 3,673,541 A * 6/1972 Volinskie ................ F16L 39/00
439/195
3,856,375 A * 12/1974 Muench ............... H01R 13/623
439/151
(Continued)

FOREIGN PATENT DOCUMENTS

AU 2005/200527 A1 2/2005
CN 2548279 Y 4/2003
(Continued)

OTHER PUBLICATIONS

Dec. 24, 2020 Office Action issued in Chinese Patent Application No. 201780011347.8 .
(Continued)

*Primary Examiner* — Harshad C Patel
(74) *Attorney, Agent, or Firm* — Oliff PLC

(57) ABSTRACT

A surgical device multi-socket for a high-frequency generator for connecting an electro-surgical instrument, an electro-surgical high-frequency generator, an electro-surgical device plug and an electro-surgical system. The invention also relates to a cable for an electro-surgical instrument and an electrosurgical instrument. In particular, the invention relates to a surgical device multi-socket for a high-frequency generator for connecting an electro-surgical instrument, in particular a bipolar applicator, including a coaxial socket which is designed to accommodate the coaxial plug element, and a first contact opening which is designed to accommo-
(Continued)

Figure 1A:
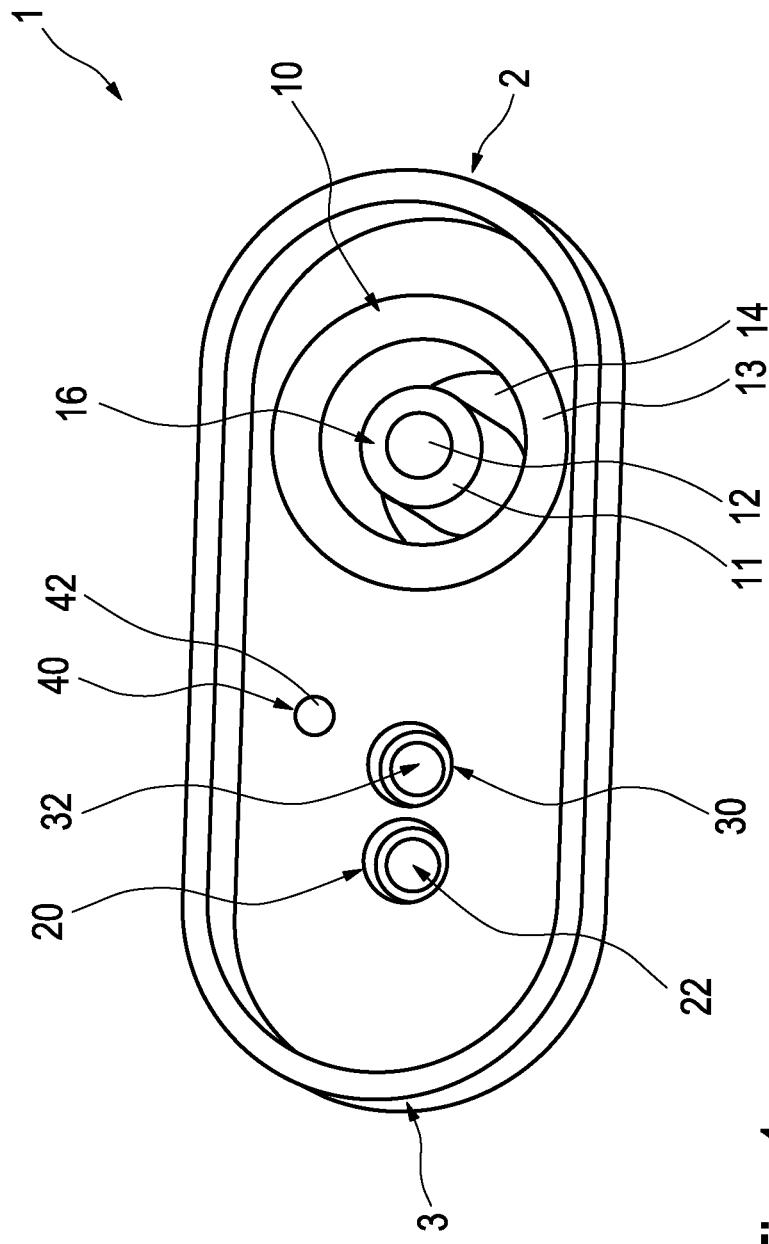
Figure 1B:
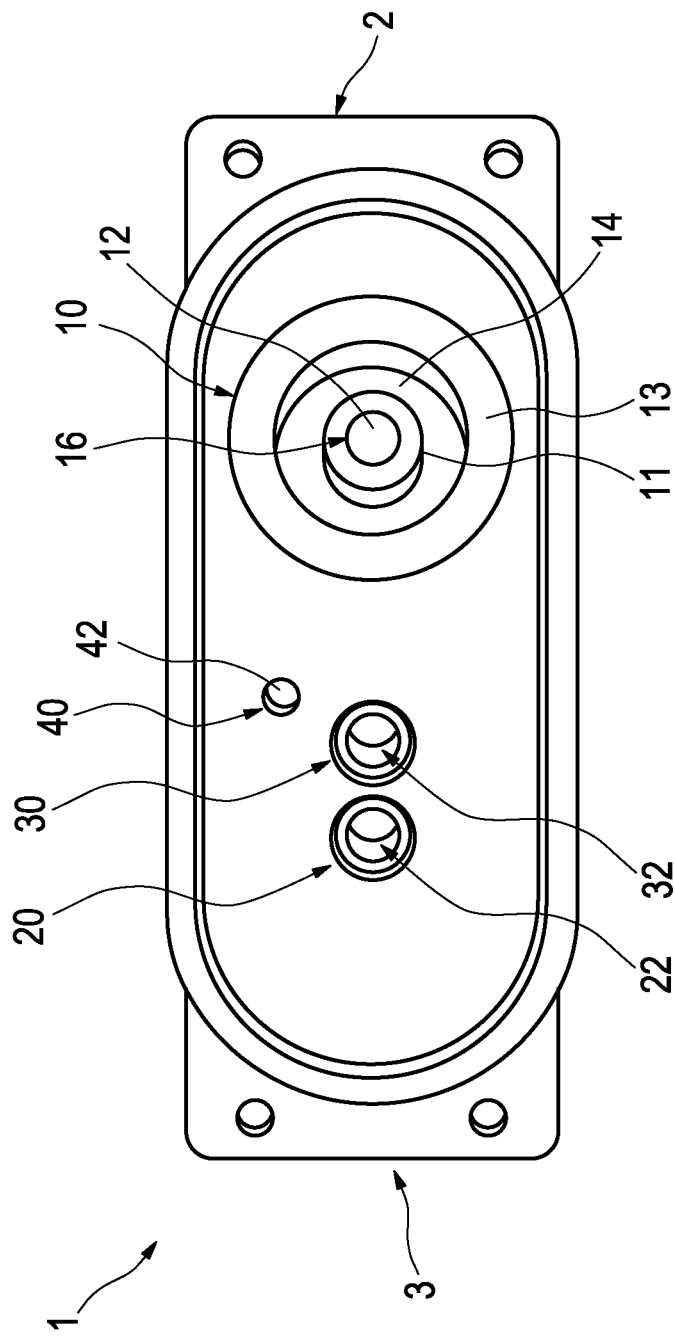
Figure 1C:
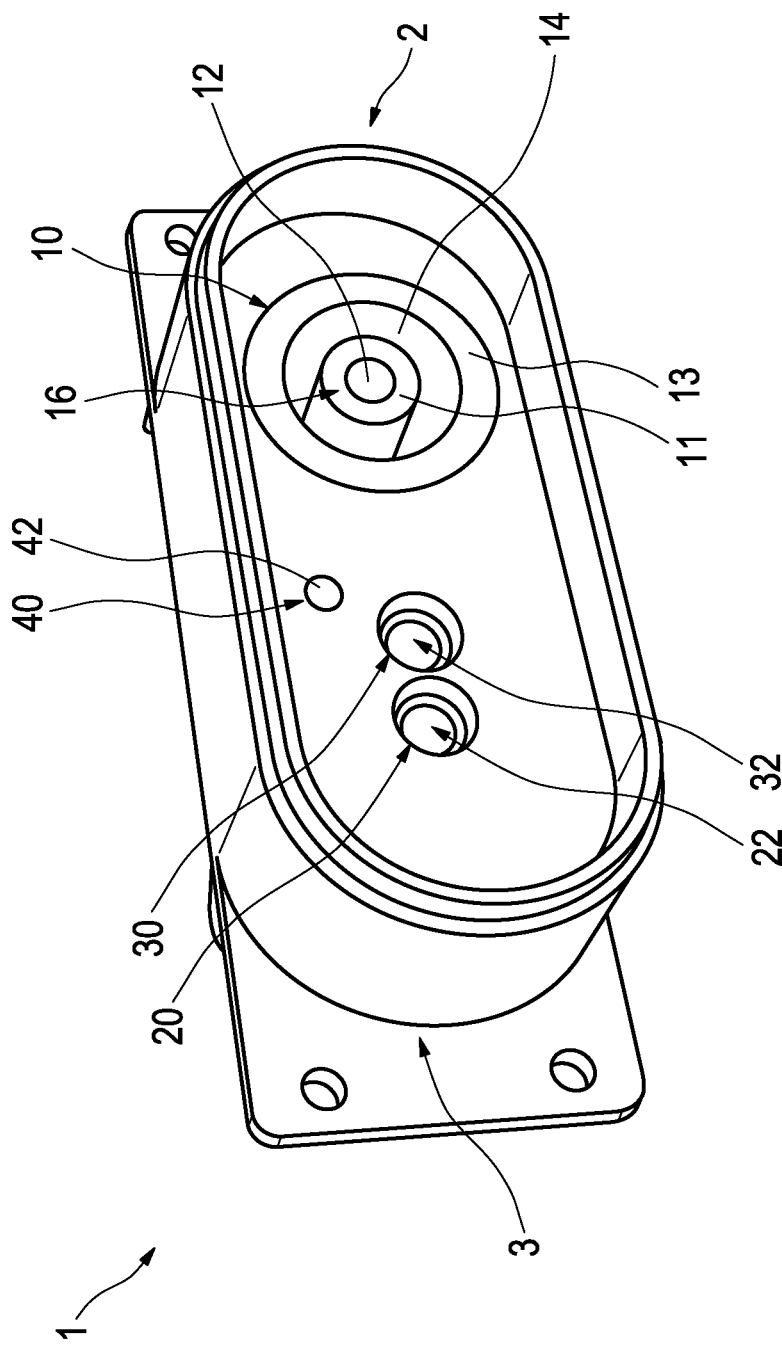
Figure 1D:
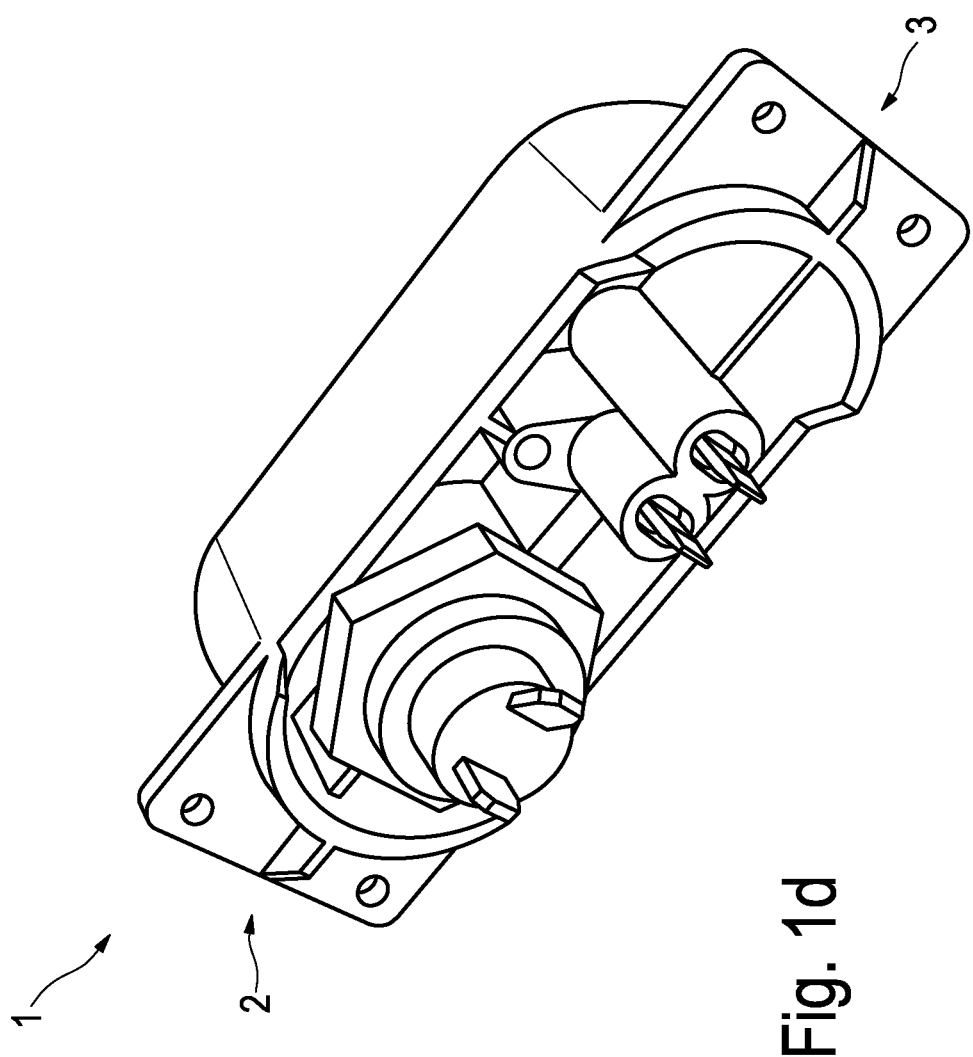

date a contact pin, and/or a second contact opening which is designed to accommodate a contact pin.

15 Claims, 20 Drawing Sheets

(51) Int. Cl.
  *H01R 27/02* (2006.01)
  *A61B 18/00* (2006.01)
  *H01R 24/40* (2011.01)
  *H01R 24/76* (2011.01)
(52) U.S. Cl.
  CPC ............... *A61B 2018/00178* (2013.01); *A61B 2018/1253* (2013.01); *H01R 24/40* (2013.01); *H01R 24/76* (2013.01); *H01R 2201/12* (2013.01)
(58) Field of Classification Search
  USPC .......................................................... 439/578
  See application file for complete search history.

(56) References Cited

U.S. PATENT DOCUMENTS

| | | | | |
|---|---|---|---|---|
| 5,211,581 A * | 5/1993 | Schwartz | ............... | H01R 24/52 439/581 |
| 5,637,006 A * | 6/1997 | Almeras | ............... | H01R 13/005 439/191 |
| 5,817,092 A | 10/1998 | Behl | | |
| 6,144,561 A * | 11/2000 | Cannella, Jr | ......... | H05K 7/1447 361/788 |
| 6,746,284 B1 * | 6/2004 | Spink, Jr. | ............. | H01R 13/115 439/651 |
| 7,121,884 B2 * | 10/2006 | Osada | ................... | H01R 13/506 439/582 |
| 7,465,177 B2 * | 12/2008 | Wood | ................... | H01R 13/005 439/191 |
| 7,704,077 B1 * | 4/2010 | Morley | ................... | H01R 24/50 439/63 |
| 8,282,415 B1 * | 10/2012 | Foltz | ..................... | H01R 13/514 439/579 |
| 8,449,318 B2 * | 5/2013 | Beller | ..................... | A61B 18/14 439/489 |
| 9,496,668 B1 * | 11/2016 | Baker | ................... | H01R 25/006 |
| 9,595,790 B1 * | 3/2017 | Cao | ................... | H01R 13/62911 |
| 9,882,317 B1 * | 1/2018 | Lane | ..................... | H01R 24/20 |
| 10,608,392 B2 * | 3/2020 | Duan | ................ | H01R 13/6588 |
| 10,932,705 B2 * | 3/2021 | Muhsin | ............... | G06F 13/4282 |
| 2002/0070702 A1 * | 6/2002 | Ragnarsson | .......... | H02J 7/0045 320/101 |
| 2004/0097912 A1 * | 5/2004 | Gonnering | ............. | H01R 31/06 606/34 |
| 2011/0045680 A1 * | 2/2011 | Beller | ..................... | A61B 18/14 439/188 |
| 2012/0095453 A1 * | 4/2012 | Cox | ......................... | A61B 18/14 606/33 |
| 2012/0202388 A1 | 8/2012 | Selig et al. | | |
| 2013/0288500 A1 | 10/2013 | Munkelt | | |
| 2014/0018802 A1 | 1/2014 | Whitman | | |
| 2015/0157054 A1 * | 6/2015 | Liu | ........................ | A24F 40/485 131/329 |
| 2015/0208728 A1 * | 7/2015 | Lord | ......................... | A24F 7/00 131/329 |
| 2016/0235120 A1 * | 8/2016 | Liu | ........................ | A24F 40/485 |
| 2018/0184712 A1 * | 7/2018 | Fraser | ................... | A24F 40/465 |

FOREIGN PATENT DOCUMENTS

| | | |
|---|---|---|
| CN | 200972903 Y | 11/2007 |
| CN | 101902979 A | 12/2010 |
| CN | 102723645 A | 10/2012 |
| CN | 202817435 U | 3/2013 |
| CN | 103378443 A | 10/2013 |
| DE | 10 2007 061 483 A1 | 7/2009 |
| EP | 2 537 480 A1 | 12/2012 |
| JP | 2000-500356 A | 1/2000 |
| JP | 2005-521465 A | 7/2005 |
| JP | 2007-521049 A | 8/2007 |
| WO | 02/085230 A2 | 10/2002 |
| WO | 2009/071256 A1 | 6/2009 |

OTHER PUBLICATIONS

May 29, 2017 Search Report issued in International Patent Application No. PCT/EP2017/053400.
May 29, 2017 Written Opinion issued in International Patent Application No. PCT/EP2017/053400.
Oct. 24, 2016 Office Action issued in German Patent Application No. 10 2016 102 640.9.
ERBE Elektromedizin GmbH: Das VIO-Kompaktgerät für die chirurgische Praxis.
Jun. 7, 2021 Office Action issued in Chinese Patent Application No. 201780011347.8.
Jan. 6, 2021 Decision to Grant issued in Japanese Patent Application No. 2018-543134.

\* cited by examiner

SURGICAL DEVICE MULTI-SOCKET, ELECTRO-SURGICAL HIGH-FREQUENCY GENERATOR, ELECTRO-SURGICAL DEVICE PLUG AND ELECTRO-SURGICAL SYSTEM

The invention relates to a surgical device multi-socket for a high-frequency generator for connecting an electro-surgical instrument, an electro-surgical high-frequency generator, an electro-surgical device plug and an electro-surgical system. The invention also relates to a cable for an electro-surgical instrument and an electro-surgical instrument.

Electro-surgical instruments are used in surgery in particular for the monopolar or bipolar cutting and/or coagulation of biological tissue. The energy for the electro-surgical instrument is provided by a high-frequency (HF) generator. Various electro-surgical instruments respectively providing the same or different functionalities to the user can be connected to such a high-frequency generator. The connected electro-surgical instruments are supplied with high-frequency energy by the high-frequency generator.

In order for the electro-surgical instruments to be able to be connected to the high-frequency generator, currently used high-frequency generators generally have different sockets for the different types of plugs of the electro-surgical instruments. Therefore, in practice, it is common for high-frequency generators to have different sockets, so that no adapters need to be available for the individual electro-surgical instruments. Surgical device plug systems are for example known from DE 10 2007 061 483 A1. In the known device plug systems, openings, in particular for the contact pins, are provided at the socket, wherein the functionality of the socket is enhanced, for example by means of coding openings. This makes it possible to transmit for example data in addition to the transmission of electrical current.

The existing sockets, devices as well as methods of connecting electrosurgical instruments to high-frequency generators offer various advantages, but further improvements are desirable.

It is therefore the object of the present invention to provide a surgical device multi-socket for a high-frequency generator for connecting an electro-surgical instrument, an electro-surgical high-frequency generator, an electro-surgical device plug and an electro-surgical system, which are improved compared to existing sockets, devices and methods. It is, in particular, an object of the present invention to provide a surgical device multi-socket for a high-frequency generator for connecting an electro-surgical instrument, an electro-surgical high-frequency generator, an electro-surgical device plug and an electro-surgical system which increase the compatibility of the used devices and/or ensure an improved safety situation before, during and after a surgical procedure.

Pursuant to a first step of the invention, this object is achieved by means of a surgical device multi-socket for a high-frequency generator for connecting an electro-surgical instrument, in particular a bipolar applicator, comprising a coaxial socket which is designed to accommodate a coaxial plug element, and a first contact opening which is designed to accommodate a contact pin, and/or a second contact opening which is designed to accommodate a contact pin.

The surgical device multi-socket pursuant to the invention is, inter alia, based on the insight that, in practice, there is a plurality of different electro-surgical instruments and, moreover, a plurality of different plugs for these electro-surgical instruments. This has the result that high-frequency generators with a plurality of different sockets are provided so that the electro-surgical instruments, which have different plugs, can be connected to the high-frequency generator. Consequently, a reduction of the overall size of the high-frequency generator is only possible to a limited extent, since a not insignificant surface area of the high-frequency generator must be reserved for the provision of the sockets. Especially the front and side surfaces of the high-frequency generator which are accessible to the user can only be reduced or be used for other purposes, for example displays or similar, to a limited extent, since the provision of the different sockets takes up a large amount of space.

A reduction of this space can only be achieved subject to a limitation of the compatibility of the high-frequency generator, namely through a reduction of the number of available sockets. However, this means that a smaller number of electro-surgical instruments can be connected to the high-frequency generator. In particular, the user will be limited in its freedom to choose the instrument manufacturer, since manufacturers usually focus on a certain plug for their electro-surgical instruments. Another option for increasing the compatibility is the provision of adapters, wherein their use during surgical operations has a plurality of disadvantages, such as the loss of adapters and the use of a non-suitable adapter for a specific electro-surgical instrument or the limitation of data transmission due to the adapter.

By combining a coaxial socket element with at least one contact opening, the surgical device multi-socket allows for a connection of both coaxial plugs and of plugs with two contact pins, the distance between which corresponds to the inner opening of the coaxial socket element of the contact opening. This, alone means, that the surgical device multi-socket allows for the combination of two, so far separate, sockets and, therefore, for the accommodation of two different plugs in one and the same socket. In this context, different plugs are preferably not accommodated by the surgical multi-socket simultaneously, but respectively when the respective plug is needed, wherein the plug that is not needed is preferably removed from the surgical device multi-socket beforehand.

In the present case of application, the plug to be respectively inserted into the surgical device multi-socket is preferably a component of an electro-surgical instrument for connecting the latter to a high-frequency generator. The surgical device multi-socket comprises, inter alia, the coaxial socket which is, in particular, designed to accommodate a coaxial plug element. A coaxial socket serves, in particular, the purpose of accommodating a coaxial cable as well as of forming a detachable connection between one end of the cable at which the coaxial plug element is arranged and the coaxial socket.

The coaxial socket comprises an inner and an outer sleeve which are arranged coaxially and preferably in a telescopic manner. The outer diameter of the inner sleeve has preferably smaller dimensions than the inner diameter of the outer sleeve. The inner diameter of the outer sleeve is preferably larger than the outer diameter of the inner sleeve. The outer diameter of the outer sleeve is preferably twice as large than the outer diameter of the inner sleeve. Furthermore, the front sides of the two sleeves are located at the proximal end of the coaxial socket, preferably essentially on a joint plane.

Between the inner and the outer sleeve, an outer, ring-shaped coaxial socket opening is formed. On the inside of the inner sleeve, an inner coaxial socket opening is formed.

The coaxial opening is, in particular, designed to accommodate a coaxial plug element, wherein the coaxial plug element comprises an inner contact pin and an outer contact ring. The outer contact ring has an inner recess, in which the inner contact pin is arranged. Thus, the outer contact ring has along the complete—or sections of its—axial extension the geometry of a sleeve. This means, if the individual dimensions are chosen correctly, a coaxial plug connection between the coaxial socket and the coaxial plug element can be achieved by inserting the inner contact pin into the inner coaxial socket opening and the outer contact ring into the outer, ring-shaped coaxial socket opening. The thus obtained coaxial plug connection has the advantage of having very little electromagnetic impact and radiation as well as of providing good electric shielding. Furthermore, there is the option to use the coaxial socket as a contact opening, by inserting the contact pin into the inner coaxial socket opening of the coaxial socket.

Furthermore, the surgical device multi-socket comprises the first contact opening and/or the second contact opening, which are respectively designed to accommodate a contact pin. In this context, the first and/or second contact opening preferably has a circular cross-section. Alternatively, the first and/or second contact opening preferably has an oval or angular cross-section, wherein, in this case, the corresponding contact pins also have such geometry.

The first and/or second contact opening comprises a connection end, where a contact pin can be inserted. At this connection end, the first and/or second contact opening has a defined diameter.

Pursuant to the invention, the coaxial socket as well as the first and/or second contact opening are arranged at an individual surgical device multi-socket. This arrangement makes it possible to connect different plugs to the multi-socket. The plugs may, for example, differ in the number and/or type of and/or distance between the contact elements, such as contact pins and/or contact rings. The plugs may, for example, differ with regard to the contact elements for the coaxial plug element. Furthermore, there is the option that the plugs might differ with regard to the contact pins which are designed to be inserted into the first and/or second contact opening, for example with regard to the diameter and/or with regard to the geometry.

In case of the surgical device multi-socket, the coaxial socket has two different functions. On the one hand, it is the function of the coaxial socket to accommodate a coaxial plug element. On the other hand, it is the task of the coaxial socket to accommodate a common contact pin in the inner coaxial socket opening formed by the inner sleeve. This allows for the option of inserting a plug with two contact pins into the surgical device multi-socket in such a way that one contact pin fits into the inner coaxial socket opening and the other contact pin fits into one of the contact openings. This double use of the coaxial socket allows for a reduction of the total number of necessary contact openings at the surgical device multi-socket and for an optimization of surface area use and compatibility.

Furthermore, it has turned out to be advantageous that, in case of an arrangement of the contact opening(s) and the coaxial socket pursuant to the invention, the risk caused by improperly connected electro-surgical instruments can be reduced. The reason for this is, in particular, that only one single electro-surgical instrument can be connected to the surgical device multi-socket pursuant to the invention. Thus, any unintended simultaneous connection of potentially incompatible devices, which might endanger the personnel and/or the patient, can be excluded. Even when instruments are switched, it is therefore ensured that a new instrument will only be able to be operated once the other instrument has been safely detached from the high-frequency generator, which also increases the safety of personnel and patients. Additional assessment steps for verifying that no other, potentially incompatible, devices are connected may be omitted in the case of a high-frequency generators with the surgical device multi-socket so that treatment times can be reduced.

Furthermore, it has turned out to be an advantage that the arrangement of the coaxial socket as well as of the first and/or second contact opening in or, respectively, at the surgical device multi-socket pursuant to the invention allows for the option to connect a plurality of different electro-surgical instruments. Thus, the user is enabled to choose from a plurality of electro-surgical instruments on the market. In a preferred embodiment of the surgical device multi-socket, the latter comprises a positioning opening configured to accommodate a positioning pin. Preferably, the positioning opening does usually not offer any electronic function or any primary electronic function, respectively, but primarily serves the purpose of a safe and correct positioning of the plug in the desired position in the surgical device multi-socket. Especially in the case of plugs which, without a positioning pin, would allow for more than one positioning option in the socket, a positioning pin and a corresponding positioning opening are advantageous in order to achieve a one-to-one positioning of the plug in the surgical device multi-socket.

Along an axial extension, the cross-section of the positioning opening is preferably essentially circular. Furthermore, there is the option of the positioning opening having an oval or angular cross-section, wherein especially a rectangular and/or quadrangular cross-section is preferred.

The dimensions of this cross-section orthogonal to a longitudinal central axis, for example the diameter in case of a circular opening or the edge dimensions in case of an angular geometry, are preferably constant along the axial extension of the positioning opening. However, these dimensions may also vary along the axial extension of the positioning opening, in order to decrease, for example, towards the inside of the surgical device multi-socket. Such a design allows for the option of further improving the positioning function of the positioning opening.

The provision of a positioning opening and of a corresponding positioning pin at a plug may reduce the wear and tear at the electrical contacts, in this case, of the coaxial socket as well as of the first and/or second contact opening.

A preferred embodiment of the surgical device multi-socket requires that the coaxial socket, the first contact opening and the second contact opening are arranged in such a way that a straight line connects the centers of the coaxial socket, the first contact opening and the second contact opening. Thus, said embodiment requires that the coaxial socket and the contact opening or the contact openings are arranged in a line. Due to the fact that the line connects the center of the coaxial socket as well as the centers of the first and second contact opening it becomes clear that these openings are arranged in a line. Such an arrangement allows, in particular, for a more compact design of the surgical device multi-socket and thus, in turn, also for a more compact design of the entire high-frequency generator.

In another preferred embodiment of the surgical device multi-socket it is required that a center of the positioning opening is arranged at a distance to a straight line connecting the centers of the coaxial socket, the first contact opening and the second contact opening. Preferably, the straight line connecting the centers of the coaxial socket, the first contact opening and/or the second contact opening does not run through the center of the positioning opening. The positioning opening is therefore preferably not arranged in a line with the electrically active connections of the surgical device multi-socket. This positioning opening not arranged in the line has the special advantage that it improves a safe and clear positioning of the plug.

A particularly preferred embodiment of the surgical device multi-socket requires that the positioning opening is arranged off-center between the first or second contact opening and the coaxial socket. Thus, this embodiment requires that the positioning opening is not located on the straight line connecting the centers of the contact opening or the contact openings and the coaxial socket. Furthermore, this embodiment requires that the positioning opening is not located in the center between the coaxial socket and the neighboring contact opening, so that the distance to the coaxial socket is greater or smaller than the distance to the closest contact opening. Thus, there is the option of the surgical device multi-socket having very small dimensions in the direction orthogonal to the straight line connecting the centers of the coaxial socket, the first contact opening and/or the second contact opening which reduces the total surface area required and makes it possible to positively influence the design of the high-frequency generator. In addition, this embodiment has the advantage of a compact plug.

Pursuant to another preferred embodiment of the surgical device multi-socket it is required that the first and the second contact opening are arranged adjacent to each other. Thus, the first and the second contact opening are arranged in such a way that no other openings or other relevant components of the surgical device multi-socket are arranged between the first and the second contact opening. This embodiment means, in particular, that neither the coaxial socket nor, if applicable, the positioning opening is arranged on a connection line connecting the center axes of the first and second contact opening. Nevertheless, the adjacent arrangement of the contact opening preferably has the result that both openings continue to exist integrally so that the walls of the contact openings do not show any overlapping or intersection.

Pursuant to another preferred embodiment of the surgical device multi-socket it is required that a distance between a central axis of the first contact opening and a central axis of the second contact opening is multiple times smaller than a distance between the central axis of the first contact opening and a central axis of the coaxial socket, and/or a distance between the central axis of the second contact opening and the central axis of the coaxial socket, and/or a distance between a central axis of the positioning opening and the central axis of the coaxial socket, wherein, preferably, the distance between the central axis of the first contact opening and the central axis of the coaxial socket is larger than the distance between the central axis of the second contact opening and the central axis of the coaxial socket and, wherein, furthermore, the distance between the central axis of the second contact opening and the central axis of the coaxial socket is preferably larger than the distance between the central axis of the positioning opening and the central axis of the coaxial socket.

This arrangement has the result that there is an area in which the coaxial socket is arranged, and a second area in which the contact openings are arranged. While both areas have a comparably small extension, these two areas are located at a—compared to the extension of these areas—large distance from each other. In addition, this arrangement preferably has the result that the positioning opening is arranged in the area or in the vicinity of the area of the first and/or second contact opening and is located at a rather larger distance from the coaxial socket. It is preferred that the distance between the first contact opening and the coaxial socket is the largest distance between two openings at the surgical device multi-socket. In addition, it is preferred in this embodiment that the positioning opening is arranged between one of the contact openings and the coaxial socket. Furthermore, it may be preferable that the positioning opening is arranged between the area in which the coaxial socket is arranged and the area in which the contact openings are arranged.

Such an arrangement of the coaxial socket as well as of the coaxial openings is advantageous in particular with regard to the fact that this makes it possible to connect different plugs available on the market to the surgical device multi-socket. It is, in particular, possible to use a plug with two contact pins with a first distance between the contact pins and furthermore another plug with two contact pins which have a second distance between each other, wherein the second distance is for example smaller than the first distance. In addition, there is the option of using a plug of the previously mentioned design, which, in addition, has a positioning pin which can be inserted into the positioning opening of the surgical device multi-socket and thus ensures the correct positioning of the plug in the surgical device multi-socket.

In another embodiment of the surgical device multi-socket it is required that the distance between the central axis of the first contact opening and the central axis of the second contact opening is a maximum of 10 times the diameter of the first and/or second contact opening. Particularly preferable is a distance of a maximum of 7.5 times the diameter; furthermore, a distance which is a maximum of 5 times the diameter is also preferred. In another particularly preferred embodiment, the distance between the two contact openings is a maximum of 2 times the diameter of the first and/or second contact opening.

In another preferred embodiment, the distance between the contact openings is between 6 and 7 mm, preferably 6.58 mm.

In a particularly preferred embodiment of the surgical device multi-socket it is required that the central axis of the coaxial socket and the central axis of the first contact opening have a distance of 28-29 mm, in particular 28.58 mm, between each other. Such a distance allows for the use of a plug with two contact pins, the distance between the central axes of which is between 28 mm and 29 mm, preferably 28.58 mm. Plugs of this type are often used in electrosurgery, so that this embodiment in particular increases the compatibility of a high-frequency generator comprising such a surgical device multi-socket. Especially the inner coaxial socket opening as well as the distance between it and the first contact opening allows for the use of a plug as described above.

Another preferred embodiment of the surgical device multi-socket requires that the distance between the central axis of the coaxial socket and the central axis of the second contact opening is 21-23 mm, in particular 22 mm. Such a distance between the coaxial socket and the second contact opening allows for the use of a plug which has two contact pins with a distance of 21-23 mm, in particular 22 mm, between each other. Such plugs with contact pins with the above mentioned distance between each other are also often used in electrosurgery.

This arrangement of the coaxial socket and the second contact opening as well as the previously described arrangement of the coaxial socket and the first contact opening show the flexibility of the presently described surgical device multi-socket. Through the compact arrangement of the coaxial socket as well as of the first and second contact opening, a plug with a contact pin distance of 21-23 mm as well as a plug with a contact pin distance of 28-29 mm as well as a coaxial plug element are able to be connected to this compact surgical device multi-socket. In addition, it becomes clear that the above described arrangement does not allow for the accommodation of more than one plug and thus for the connection of more than one electro-surgical instrument to the surgical device multi-socket. This leads to a significantly better safety situation, since wrong connections or unintended multiple connections are not possible.

Pursuant to another embodiment of the surgical device multi-socket it is required that the coaxial socket has a connection end into which a coaxial plug element can be inserted, and/or that the first contact opening has a connection end into which a contact pin can be inserted, and/or that the second contact opening has a connection end into which a contact pin can be inserted, and/or that the positioning opening has a connection end into which a positioning pin can be inserted, wherein at least two connection ends are located on a joint plane.

The connection ends of the contact openings and/or the coaxial socket and/or the positioning opening must, in particular, be understood in such a way as to mean that at them an element to be inserted can enter and/or be inserted. Located on a joint plane means, in particular, that the orthogonal lines at the connection end create a two-dimensional geometry and/or a plane from parallel central axis of the contact openings and/or the positioning opening and/or the coaxial socket. In a preferred version of this embodiment it is required that at last three connection ends are located on a joint plane and, alternatively, it is preferably required that all the connection ends are located on a joint plane. An arrangement of three or more connection ends on a joint plane is advantageous due to the fact that a particularly compact design of the surgical device multi-socket can be achieved.

Pursuant to another aspect of the invention, the above mentioned object is achieved by means of a surgical device multi-socket for a high-frequency generator for connecting an electro-surgical instrument, in particular a monopolar applicator, comprising a coaxial socket which is designed to accommodate a coaxial plug element, and a first contact opening which is designed to accommodate a contact pin, and a second contact opening which is designed to accommodate a contact pin, and a third contact opening which is designed to accommodate a contact pin, wherein preferably the centers of the first contact opening and the second contact opening and the third contact opening are arranged on a straight line, and a fourth contact opening.

It is particularly preferred that the first contact opening and the second contact opening and the third contact opening are arranged in such a way that a 3-pin plug, in particular a 3-pin plug with a 4 mm contact pin diameter, can be connected to the surgical device multi-socket by means of the first contact opening and the second contact opening and the third contact opening by arranging the contact pins of the three-pin plug in the first contact opening, the second contact opening and the third contact opening. Thus, the compatibility of the surgical device multi-socket is further increased by making it possible to connect in this embodiment a 3-pin plug, with three contact pins, in addition to the one-pin and two-pin plugs with one or, respectively, two contact pins. Furthermore, the connection of special plugs, for example for maintenance purposes, is facilitated due to the fact that the maintenance plug is designed for a defined contact opening combination.

In another preferred embodiment of the surgical device multi-socket it is required that the fourth contact opening and one, two or several further contact openings respectively have a diameter orthogonal to a plug in direction, wherein the one, two or several further contact openings are chosen from the group consisting of the first contact opening and the second contact opening and the third contact opening, wherein the diameter of the fourth contact opening is larger than the diameter or, respectively, the diameters of the one, two or several further contact openings, wherein the diameter of the fourth contact opening is preferably between 6 mm to 10 mm, in particular between 7.5 mm to 8.5 mm.

Preferably, the fourth contact opening has the largest diameter of the arranged contact openings, in particular in comparison with the first, second and third contact opening, wherein the coaxial socket regularly has a larger diameter at the outer circumference. The arrangement of the fourth opening allows for a particular increase of compatibility. As a result, there is the option of arranging a plurality of currently relevant plugs in the medical-technical area, while the sockets known in prior art do not provide such compatibility. On the one hand, this can lead to a reduction of the total number of sockets at a high-frequency generator, on the other, to a reduction of the costs. The reasons for the cost reduction are manifold. First of all, a smaller total number of sockets might be required which allows for a reduction of the costs and efforts during manufacture and assembly. Furthermore, the number of possible versions of high-frequency generators is reduced so that the complexity in the development area, but also in distribution, can be reduced and thus becomes better controllable. Furthermore, a client no longer has to choose between several options or choose the expensive option with a large total number of sockets.

Furthermore, it is preferred that the first contact opening and/or the second contact opening and/or the third contact opening has a diameter of 4 mm with a tolerance that is common in the area of relevant plug connections, in particular a tolerance of plus 0.1 mm and minus 0.1 mm. In addition, the diameter of the fourth contact opening may be 8 mm, with a tolerance that is common in the area of relevant plug connections, in particular a tolerance of plus 0.1 mm and minus 0.1 mm.

A preferred embodiment of the surgical device multi-socket requires that the coaxial socket and/or the fourth contact opening is or, respectively, are arranged between the second contact opening and the third contact opening. With regard to the direction of a connection line connecting the centers of the first contact opening and the second contact opening and the third contact opening, the coaxial socket and/or the fourth contact opening is or, respectively, are, in particular arranged between the second contact opening and the third opening. The arrangement between the second and third contact opening allows for the arrangement of a plurality of plugs, despite the fact that only a small space is required for the arrangement of the contact openings and the coaxial socket.

In another preferred embodiment of the surgical device multi-socket it is required that the coaxial socket and the fourth contact opening are arranged in such a way that a line connecting their centers is oriented orthogonally to a connection line connecting the centers of the first contact opening and the second contact opening and the third contact opening. In an operational state, the coaxial socket and the fourth contact opening are preferably arranged vertically on top of each other with regard to their centers, wherein in this case the first contact opening and the second contact opening and the third contact opening are then arranged horizontally next to each other so that the connection line connecting their centers also extends horizontally. Alternatively, in an operational state, the coaxial socket and the fourth contact opening are preferably arranged horizontally next to each other with regard to their centers, wherein in that case the first contact opening and the second contact opening and the third contact opening are then arranged vertically on top of each other so that the connection line connecting their centers also extends horizontally.

As a result of this arrangement, the required space at the generator can be kept small, with the advantage that the generator can have a particularly compact design and/or that space can be created at the generator for additional functions and/or function elements, such as screens or operating elements. This allows also for, or at least facilitates, in particular a simultaneous connection of several plugs. Furthermore, it is preferably required that the first contact opening is arranged on the side of the second contact opening which faces away from the third contact opening. Furthermore, it may be preferred that the first contact opening is arranged on the side of the second contact opening which faces away from the third contact opening.

Another preferred embodiment requires that the coaxial socket and the fourth contact opening have such a distance between each other that it is possible to simultaneously arrange a coaxial plug in the coaxial socket and a contact pin, in particular a Bovie plug, in the fourth contact opening. It is particularly preferred that the centers of the coaxial socket and the fourth contact opening are arranged at a distance from each other, wherein the distance is preferably larger than 1 time the diameter, or larger than 1.5 times the diameter, or larger than 2 times the diameter, or larger than 2.5 times the diameter, or larger than 3 times the diameter, or larger than 4 times the diameter of the fourth contact opening.

A preferred embodiment further requires that, in a mounted state, in the direction of the straight connection line, the fourth contact opening is arranged above the straight line connecting the centers of the first contact opening and the second contact opening and the third contact opening.

Furthermore, it may be preferred that, in a mounted state, in the direction of the straight connection line, the coaxial socket is arranged below the straight line connecting the centers of the first contact opening and the second contact opening and the third contact opening.

Pursuant to another aspect of the invention, the above mentioned object is achieved by means of a high-frequency generator comprising a surgical device multi-socket pursuant to one of the previously described embodiments. Such an electro-surgical high-frequency generator is, first of all, characterized in that it is compatible with a plurality of different electro-surgical instruments.

This results in a large selection of different plugs which may be used with the electro-surgical high-frequency generator. These plugs may differ on the one hand with regard to the distance between the provided contact pins, and, on the other, they may differ in that the plug may or may not have a positioning pin. In addition, the plugs may or may not have a coaxial plug element. The large selection of different plugs for electro-surgical instruments leads to the requirement for high-frequency generators that they must be able to also accommodate different plugs or to be compatible with them, respectively.

Pursuant to another aspect of the present invention, the above mentioned object is achieved by means of an electro-surgical device plug for plugging into a surgical device multi-socket pursuant to one of the previously described embodiments, comprising a coaxial plug element and at least one contact pin. Particularly preferred is such an electro-surgical device plug where the central axis of the coaxial plug element and the central axis of the contact pin are arranged at a distance of 22-23 mm from each other. Alternatively, it is preferred that the central axis of the coaxial plug element and the central axis of the contact pin are arranged at a distance of 28-29 mm from each other.

Moreover, it is preferred that the electro-surgical device plug has a positioning pin which is designed and arranged to be inserted into a positioning opening. Such a plug can reduce or, respectively, even eliminate, different disadvantages of existing plug types, wherein such a plug was not used in previous solutions, since, generally, the connection sockets in the electro-surgical high-frequency generators were not able to accommodate a plug comprising a coaxial plug element and a contact pin.

Pursuant to another aspect of the present invention, the object mentioned above is achieved by means of an electro-surgical system, comprising a high-frequency generator pursuant to one of the previously described embodiments, and an electro-surgical instrument that is or can be connected via the surgical device multi-socket of the high-frequency generator. In addition to a compact design, such a system also allows for a flexible use of different electro-surgical instruments from different manufacturers as well as of electro-surgical instruments with different plugs. In addition, it is not possible in case of the present system to create a wrong plug connection. Furthermore, the user cannot connect more than one electro-surgical instrument at a time to the high-frequency generator. This means that damage to the high-frequency generator and/or the electro-surgical system might be able to be prevented. Preferably, the electro-surgical instrument that is or can be connected to the surgical device multi-socket of the high-frequency generator has a previously described electro-surgical device plug.

Pursuant to another aspect of the present invention, the object mentioned above is achieved by means of a cable for an electro-surgical instrument, characterized in that the cable is connected to an electro-surgical device plug pursuant to one of the previously explained aspects of the invention. The cable is preferably designed as a multi-core assembly of several individual lines isolated from each other, wherein the individual lines serve, in particular, for the transmission of energy, preferably of a current, and/or for the transmission of information and/or data. In addition, the cable may also comprise an additional line for transporting fluids, for example coolant. Furthermore, the cable is preferably coated with an insulation material, wherein, as a general rule, the cable still has preferably elastic characteristics, so that the cable is bendable. The connection of the cable with the electro-surgical device plug may be designed so that it can be detached, in particular by a user, such as a plug connection, or in a non-detachable manner.

Pursuant to another aspect of the present invention, the object mentioned above is achieved by means of an electro-surgical instrument, characterized in that the electro-surgical instrument is connected to a cable pursuant to the aspect described above. A connection at the connection point between the cable and the electro-surgical instrument may be designed so that it can be detached, in particular by a user, or in a non-detachable manner. A detachable connection between the cable and the electro-surgical instrument has the advantage that only the defect component must be replaced and the intact component may be continued to be used if the cable or the instrument is defect.

A non-detachable connection means a connection which is not intended to be detached by the user. A connection that cannot be detached, in particular by the user, in turn, has the advantage that an unintended separation of the connection, especially during the use of the electro-surgical device is prevented or at least becomes more difficult so that the safety during use, in particular during a surgical operation, is increased.

Regarding the further advantages, embodiments and embodiment details of these additional aspects and their potential further developments, reference is also made to the previous description of the respective features and further developments of the surgical device multi-socket.

Figure 2:
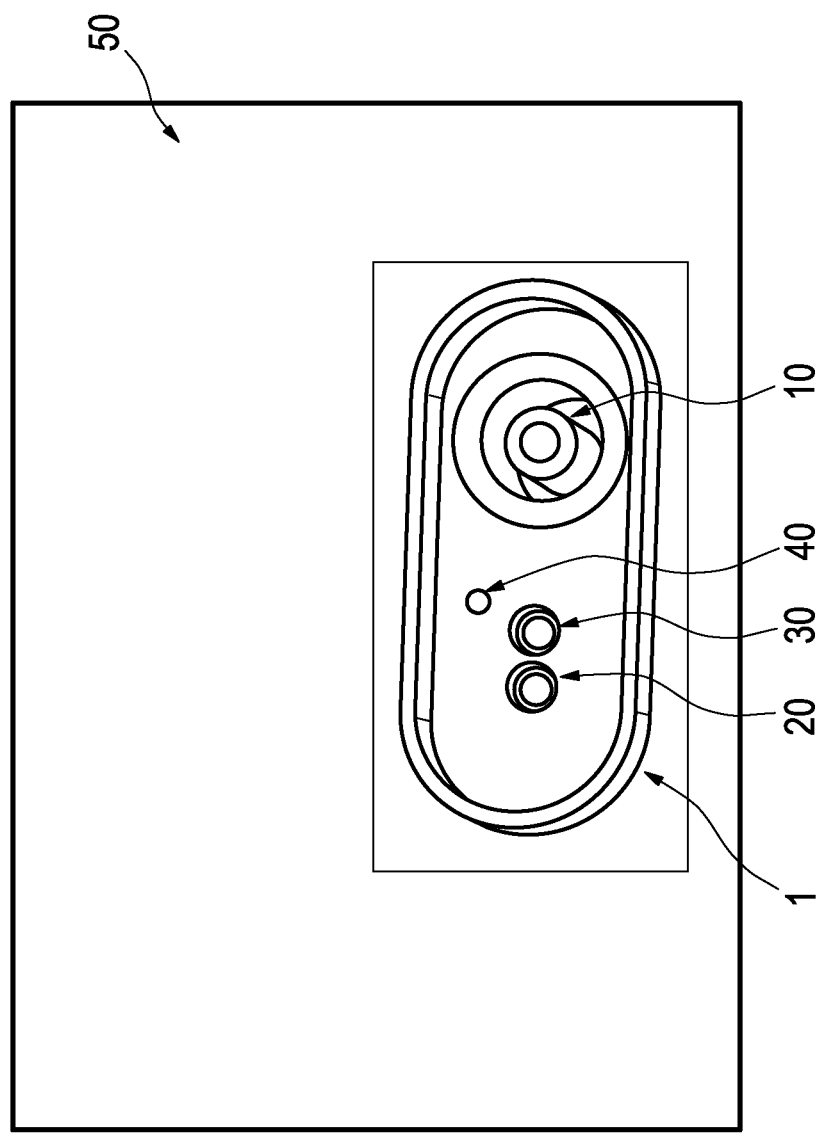
Figure 3:
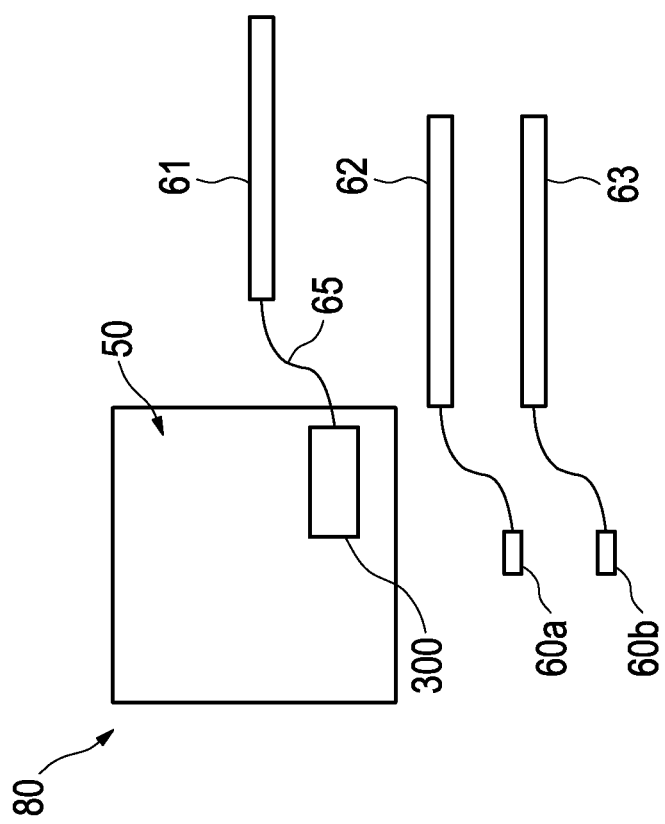
Figure 4:
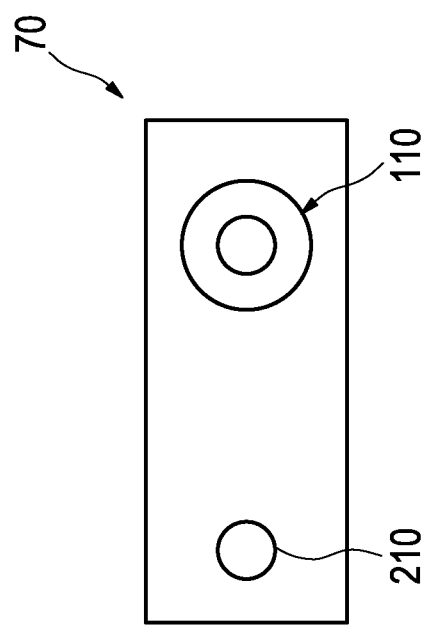

Preferred embodiments of the invention are, by way of example, described by means of the attached figures. The following is shown in FIG. 1a-1d: an exemplary embodiment of a surgical device multi-socket;

FIG. 2: a high-frequency generator with an exemplary surgical device multi-socket;

FIG. 3: an electro-surgical system with a high-frequency generator and an exemplary surgical device multi-socket;

FIG. 4: an electro-surgical device plug; and

Figure 5:
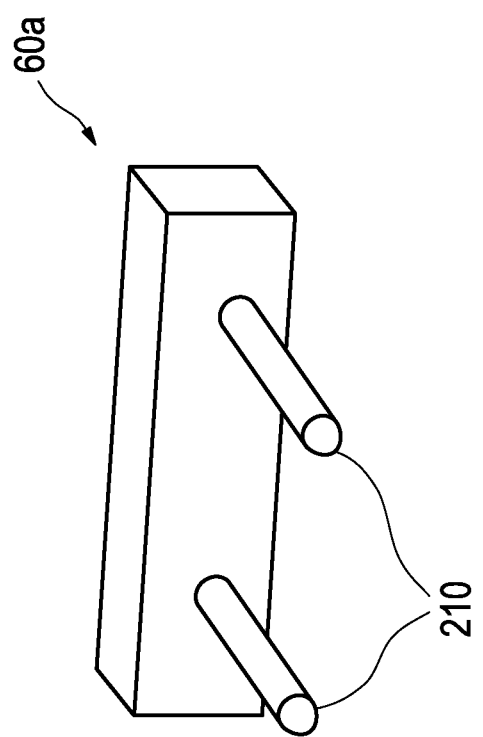

FIG. 5: a plug with two contact pins.

Figure 6:
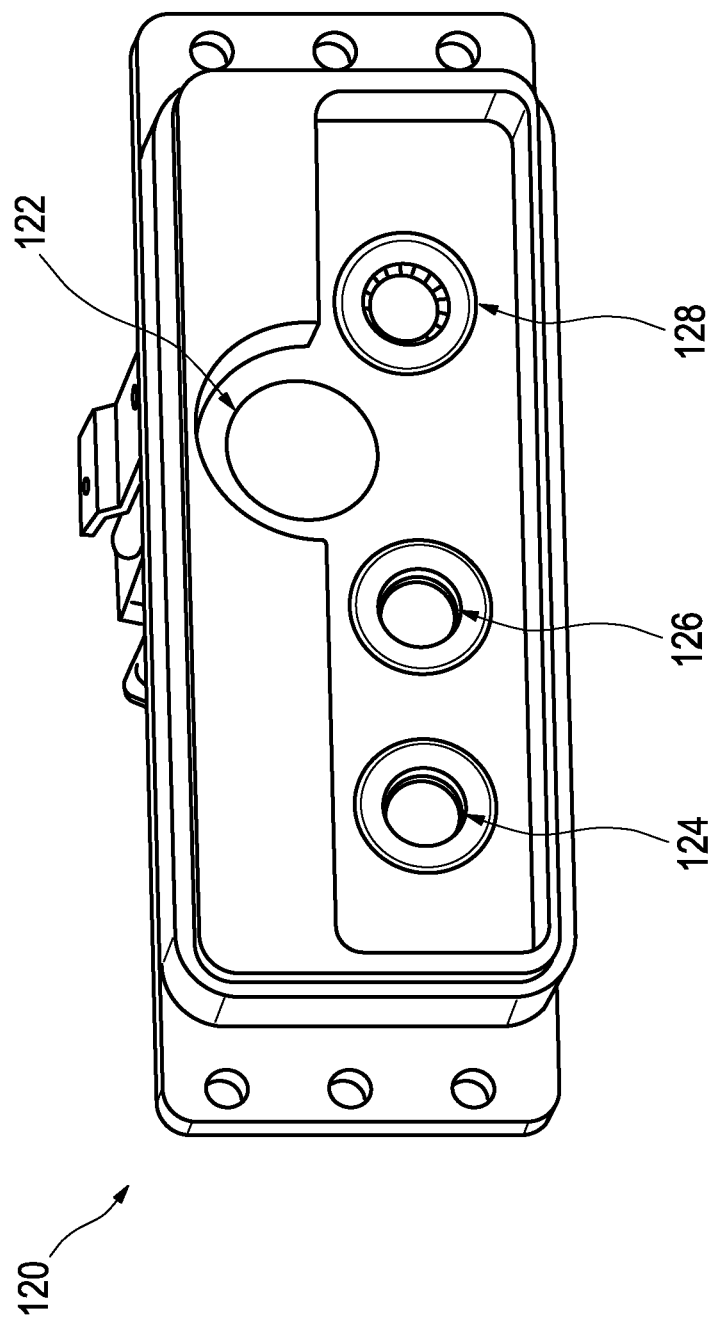
Figure 7:
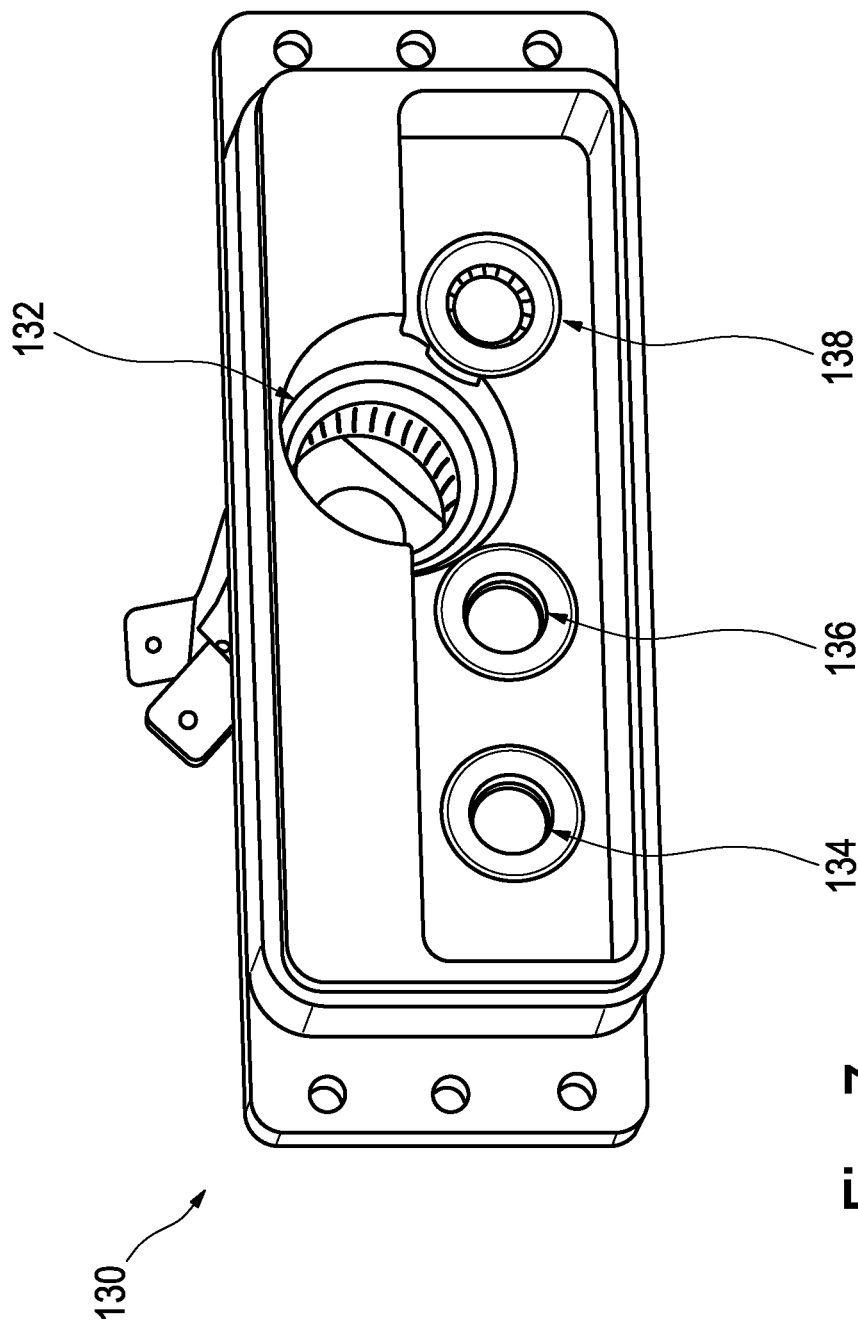
Figure 8A:
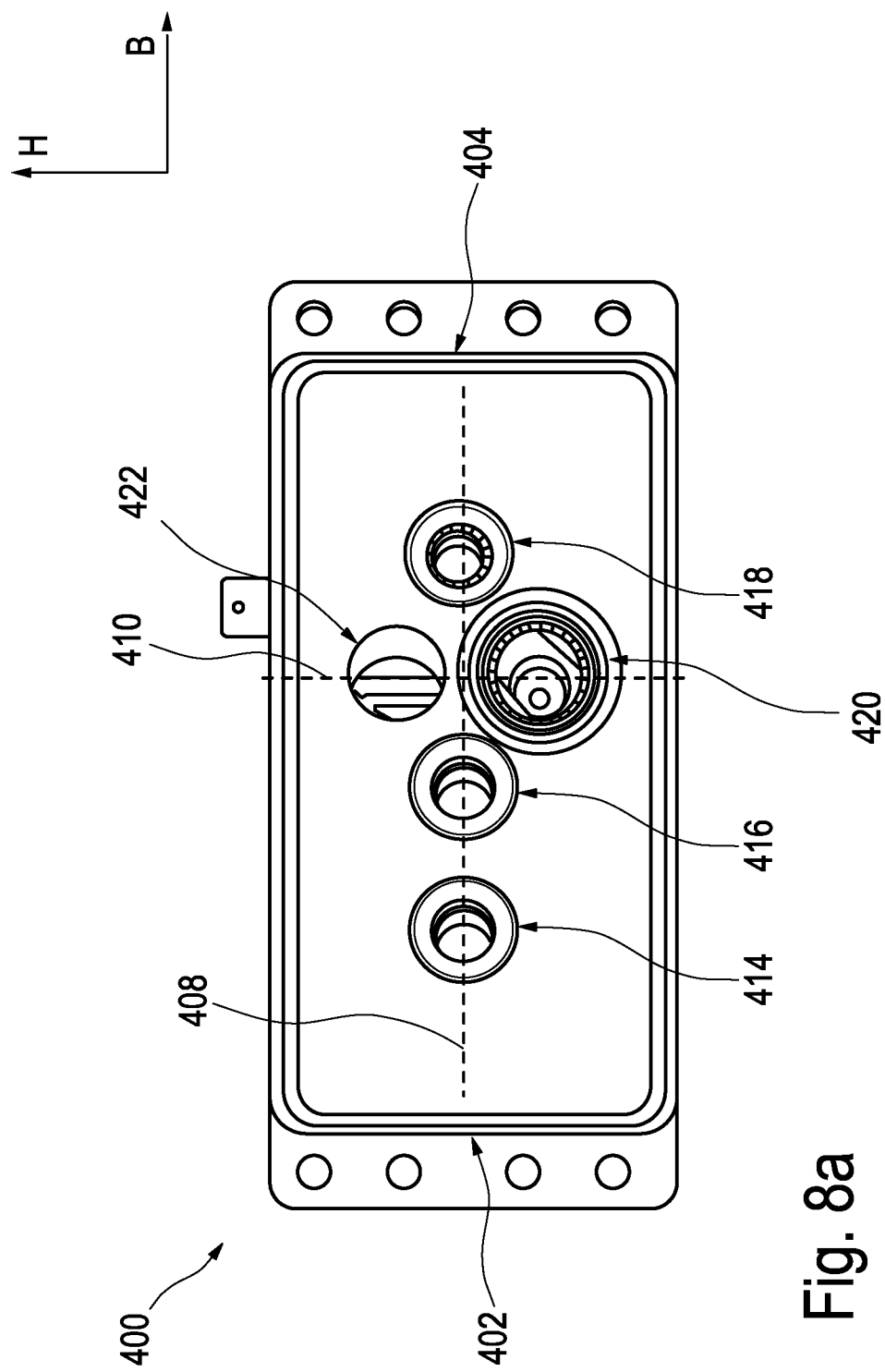
Figure 8B:
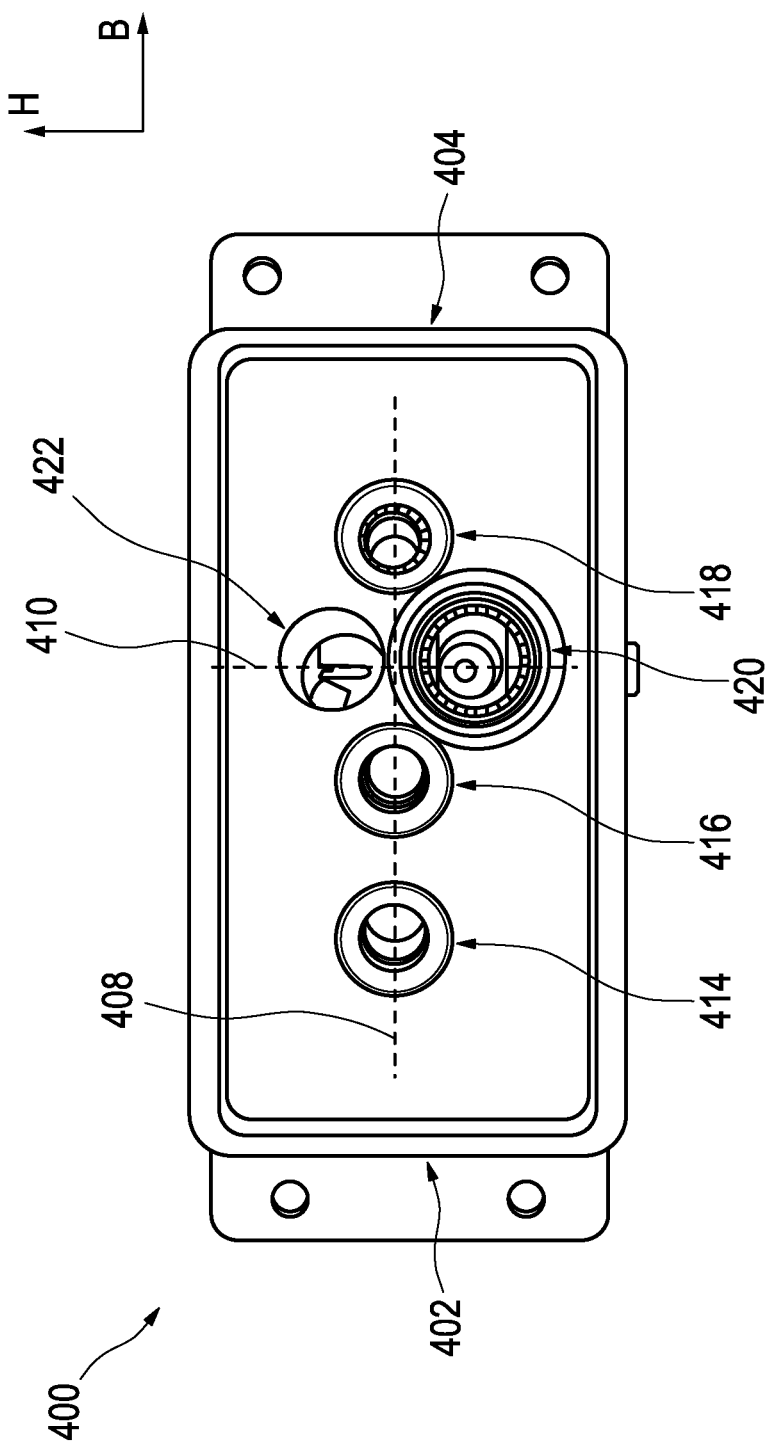
Figure 8C:
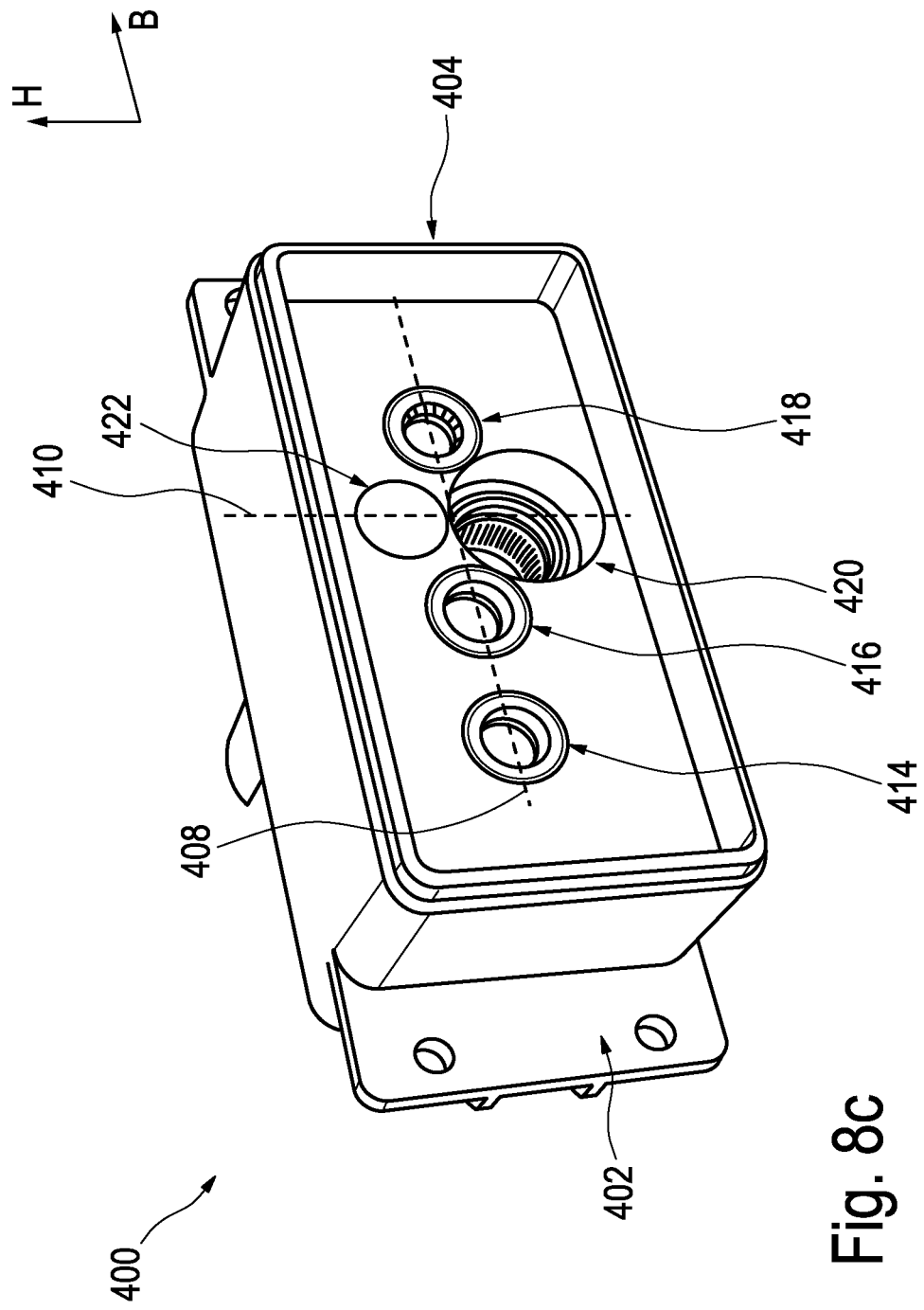
Figure 8D:
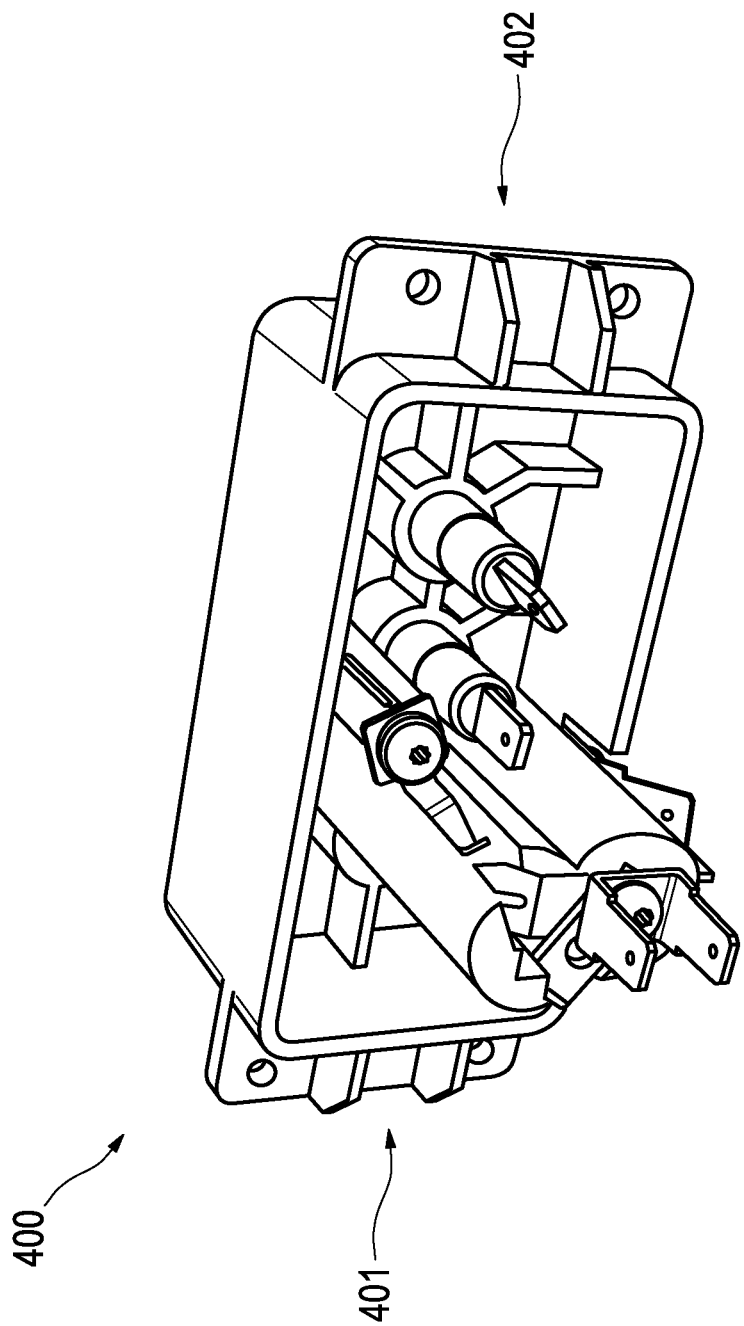
Figure 9:
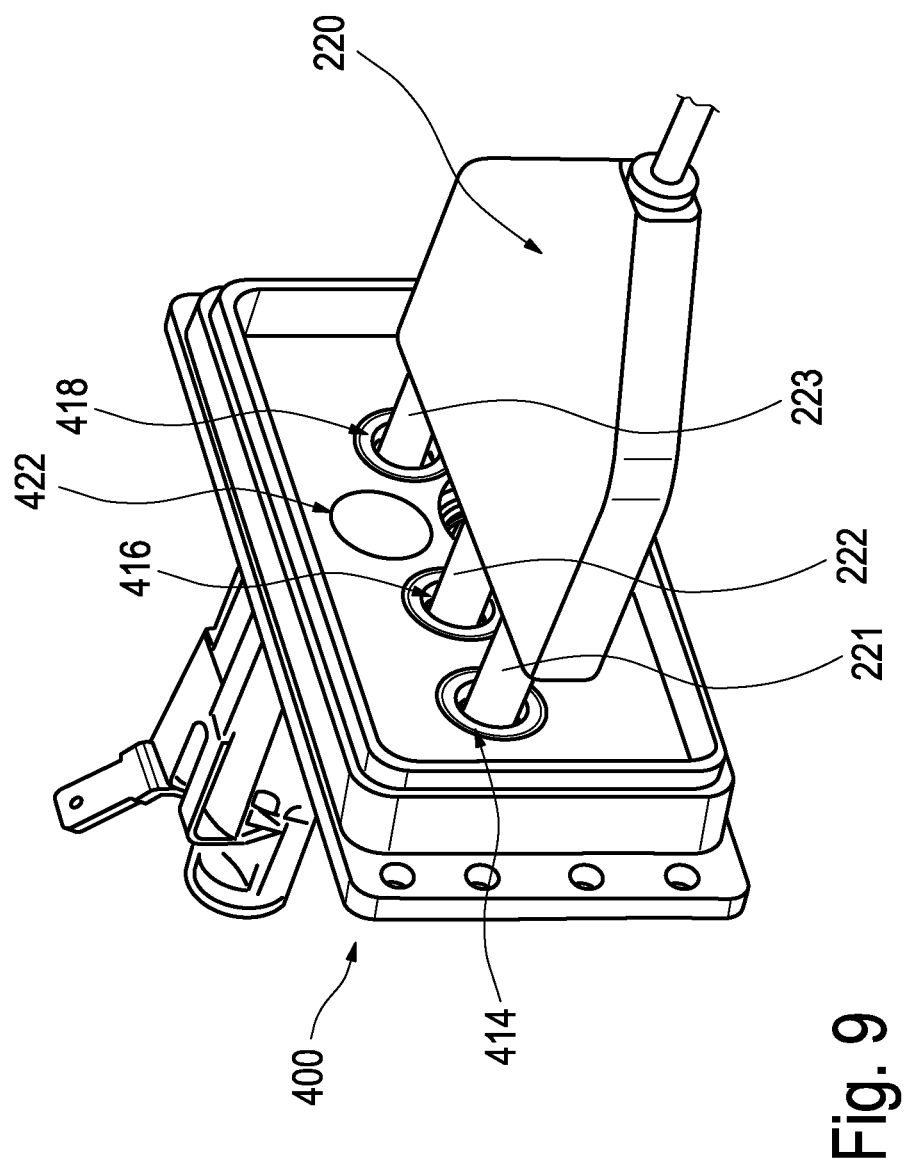
Figure 10:
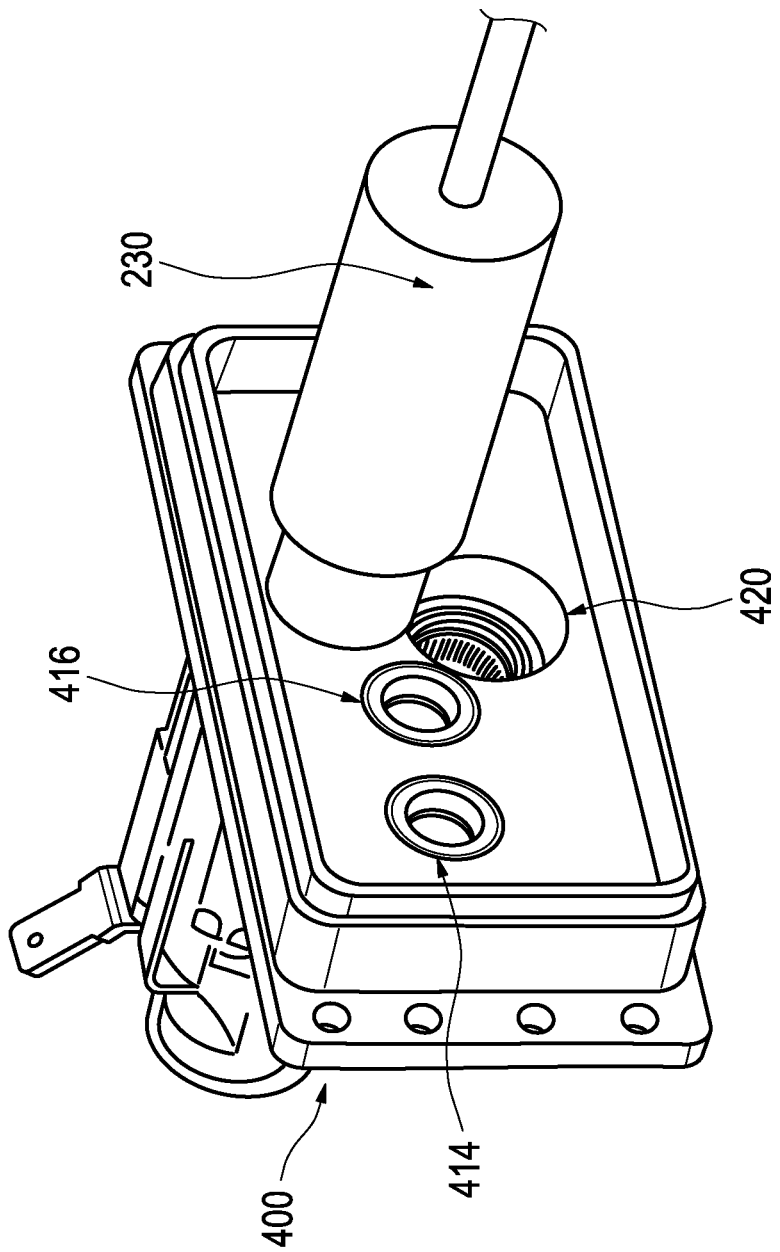
Figure 11:
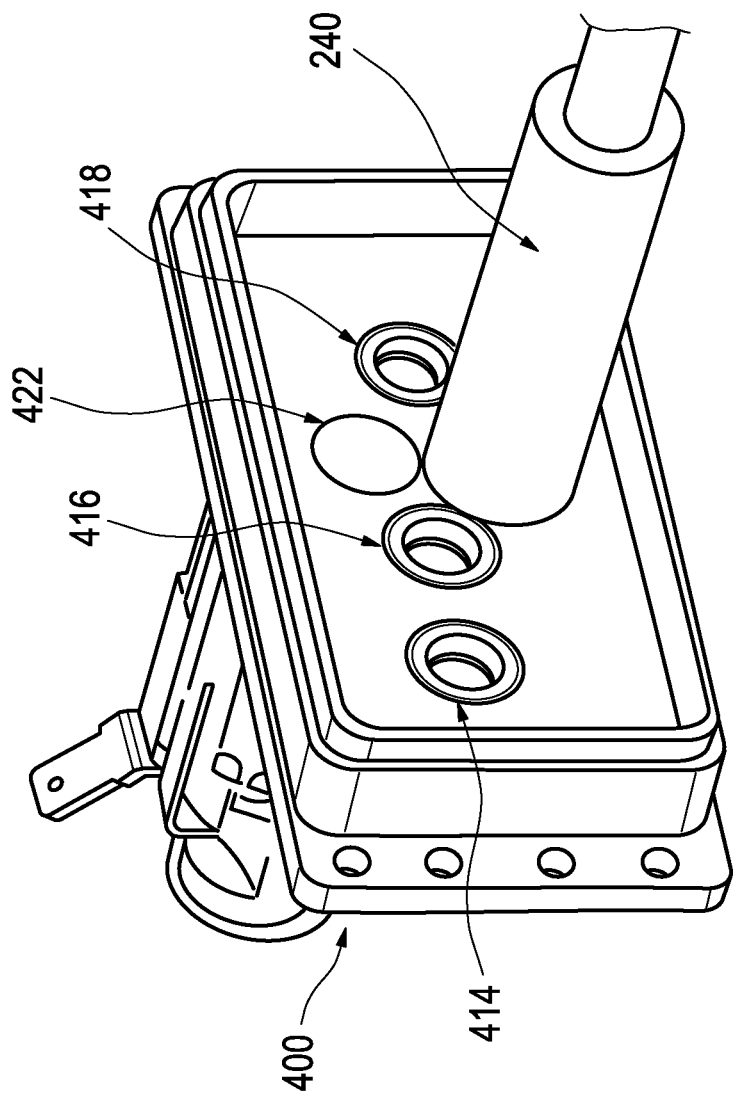
Figure 12:
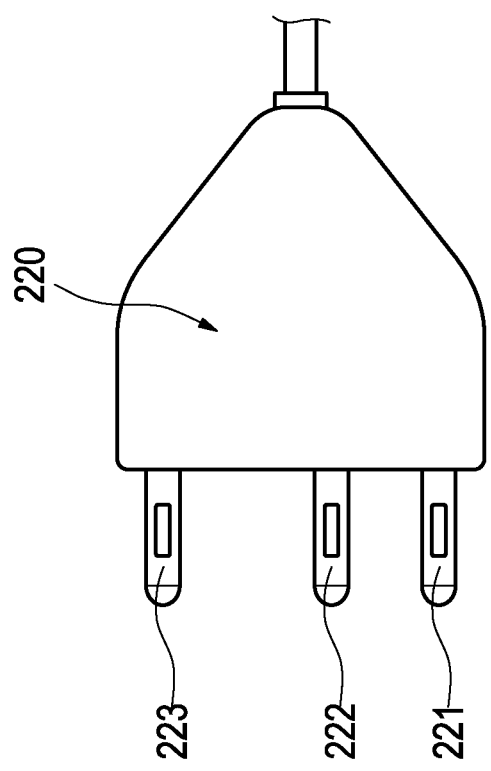
Figure 13:
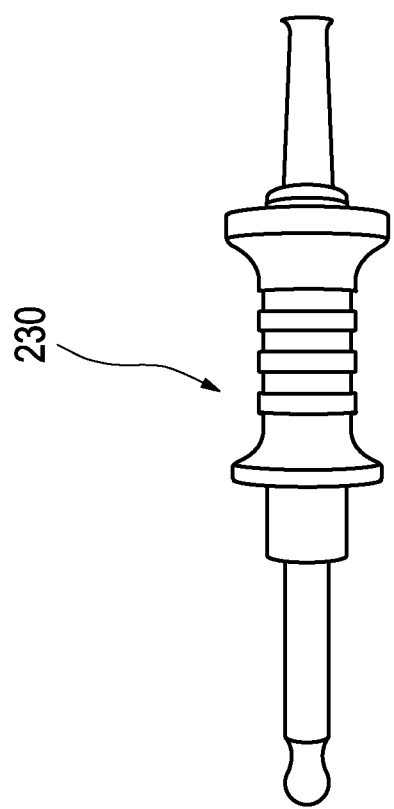
Figure 14:
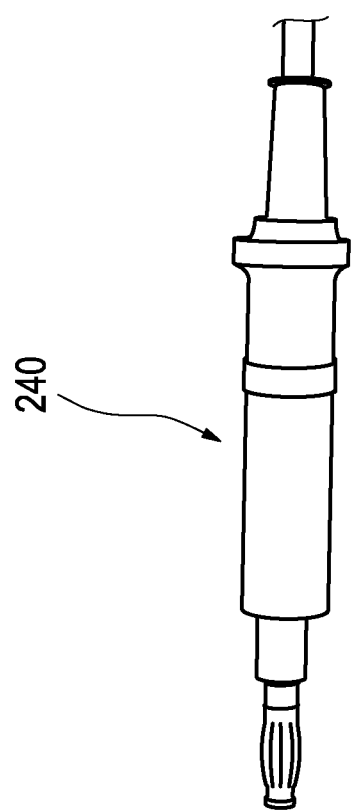

FIG. 6: a surgical device multi-socket known in prior art for a Bovie plug;

FIG. 7: a surgical device multi-socket known in prior art for a coaxial plug;

FIG. 8a-8d: another exemplary embodiment of a surgical device multi-socket;

FIG. 9: a schematic, three-dimensional view of the surgical device multi-socket with a three-pin plug shown in FIG. 8a-8d;

FIG. 10: a schematic, three-dimensional view of the surgical device multi-socket with a Bovie plug shown in FIG. 8a-8d;

FIG. 11: a schematic, three-dimensional view of the surgical device multi-socket with a coaxial plug shown in FIG. 8a-8d;

FIG. 12: a three-pin plug known in prior art;

FIG. 13: a plug with large contact pin known in prior art;

FIG. 14: a coaxial plug known in prior art.

FIGS. 1a-1d show exemplary embodiments of a surgical device multi-socket 1. The surgical device multi-socket extends from a first end 2 to a second end 3. The surgical device multi-socket 1 has flat oval outer contours, comprising two parallel sides opposite to each other, and, at the first and second end 2, 3, a bent, in particular semicircular geometry. A coaxial socket 10 is arranged in a section adjacent to the first end 2 of the surgical device multi-socket 1.

The coaxial socket 10 is formed by two coaxially arranged sleeves. The inner sleeve 11 is essentially enclosed by the outer sleeve 13 in radial direction. Furthermore, the inner sleeve 11 has an outer diameter which is smaller than the inner diameter of the outer sleeve 13. Thus, two openings are formed, which are formed by the space between the outer and the inner sleeve 13, 11 and the hollow space of the inner sleeve 11 caused by the geometry. The space between the outer and the inner sleeve 13, 11 forms the outer, ring-shaped coaxial socket opening 14 and the space created inside the inner sleeve 11 forms the inner coaxial socket opening 12.

The first contact opening 20 and the second contact opening 30 are arranged in a section adjacent to the second end 3 of the surgical device multi socket 1. The contact openings 20, 30 have a circular cross-section orthogonal to the central axis which essentially has the same diameter as the inner coaxial socket opening 12. The first contact opening 20 and the second contact opening 30 are arranged on a theoretical connection line extending from the first end 2 to the second end 3. In this case, the first contact opening 20 is facing the second end 3, and the second contact opening 30 is facing the first end 2 or the coaxial socket 10, respectively. The theoretical connection line connecting the first end 2 and the second end 3 theoretically divides the surgical device multi-socket 1 into two, horizontally separated halves, which, in vertical direction, have the same dimensions. The centers of the first contact opening 20, of the second contact opening 30 as well as of the coaxial socket 10 are located on this line.

Furthermore, the surgical device multi-socket 1 has a positioning opening 40. Orthogonally to the central axis, the positioning opening 40 has a circular cross-section. The diameter is smaller than the diameter of the contact openings 20, 30. Furthermore, the positioning opening 40 is not located on the connection line connecting the centers of the contact openings 30, 40 and of the inner coaxial socket 10, so that the positioning opening 40 is also not arranged in a line with the first and second contact openings 20, 30 or the coaxial socket 10.

The coaxial socket 10, the contact openings 20, 30 and the positioning opening 40 are essentially inserted into a flat surface of the surgical device multi-socket 1. In this context, a connection end 22 of the first contact opening 20 and a connection end 32 of the second contact opening 30 are slightly moved into this plane, so that they are recessed. The connection opening 42 of the positioning opening 40 and the connection end 16 of the coaxial socket 10 are essentially located on a plane with the previously described plane of the surgical device multi-socket 1.

FIG. 2 shows a high-frequency generator 50 with a surgery device multi-socket 1. The surgery device multi-socket 1 of this high-frequency generator 50 also comprises the above described coaxial socket 10, the first contact opening 20 and the second contact opening 30. In addition, the surgical device multi-socket 1 comprises the positioning opening 40.

FIG. 3 shows an electro-surgical system 80 with a high-frequency generator 50 and a surgical device multi-socket 300 to which a first electro-surgical instrument 61 is connected. The electro-surgical system 80 comprises the high-frequency generator 50 with a further embodiment of the surgical device multi-socket 300 as well as a first electro-surgical instrument 61. The electro-surgical instrument 61 is connected to a connection cable 65 and, via a plug (not shown) arranged at said connection cable, to the surgical device multi-socket 300. The surgical device multi-socket 300 is arranged at the high-frequency generator 50. In addition, a second electro-surgical instrument 62 and a third electro-surgical instrument 63 are available. The electro-surgical instruments 62, 63 respectively have a plug 60a, 60b, wherein the plugs 60a, 60b are preferably of different types; they may, for example, differ in the distance between the contact pins.

Furthermore, a fourth electro-surgical instrument 64 is shown, which is connected to an electro-surgical device plug 70 via a further connection cable 65a. The electro-surgical device plug 70 is shown in more detail in FIG. 4. The connection between the fourth electro-surgical instrument 64 and the connection cable 65a may be a permanent connection or a—non shown—plug connection so that the cable 65a and the electro-surgical instrument 64 are preferably provided as separate assemblies.

FIG. 4 shows an electro-surgical device plug 70. The electro-surgical device plug 70 comprises a contact pin 210 as well as a coaxial plug element 110. The coaxial plug element 110 comprises in this context a circular sleeve, wherein this sleeve has a thin-walled design. A contact pin which in turn has a circular cross-section is arranged coaxially inside this sleeve.

FIG. 5 shows a plug with two contact pins 210. FIG. 5 shows schematically a common plug 60a for an electro-surgical instrument 62 or, respectively, for connecting an electro-surgical instrument 62 via a surgical device multi-socket to a high-frequency generator 50. The plug 60a has two contact pins 210 arranged at a base element. The contact pins 210 respectively have a longitudinal extension, wherein a circular cross-section is formed orthogonally to the longitudinal extension.

An electro-surgical instrument with a plug 60a pursuant to FIG. 5 is suitable for being connected to the high-frequency generator 50 of FIG. 2. In this context, the option of using two different plugs with contact pins 210 is available. First of all, there is the option of using a plug of which one contact pin 210 is inserted into the inner coaxial socket opening 12 and the other contact pin 210 is inserted in the first contact opening 20. In addition, there is the option of using a plug of which the first contact pin 210 is also inserted into the inner coaxial socket opening 12, while the second contact pin 210, however, is inserted into the second contact opening 30 of the surgical device multi-socket 1, 300.

The previously mentioned inserting of the contact pins 210 into the openings preferably takes place simultaneously, since the contact pins 210 are arranged permanently and on one plane at a base body of the plug 60a. Due to the fact that the surgical device multi-socket 1, 300 comprises the first and second contact opening, the option of using plugs with different distances between the contact pins 210 becomes available. In addition, there is the option of using a plug which is suitable for a coaxial socket, for example a coaxial plug element 110.

Furthermore, it is possible to use, in addition to these plugs available on the market, a special electro-surgical device plug 70 which comprises a coaxial plug element 110 and at least one contact pin 210. Furthermore, there is the option of using a plug which comprises a coaxial plug element 110 and two contact pins 210, wherein, in this case, the distance between the two contact pins 210 is the same as the distance between the two contact openings 20, 30. In addition, there is the option of using a plug which comprises one of the previously mentioned embodiments, but comprises in addition a positioning pin, wherein said positioning pin is inserted into the positioning opening 40 of the surgical device multi-socket 1, 300.

Since different plugs, differing in particular with regard to the number of contact pins 210, the coaxial plug element 110 and the positioning pin (not shown), can be inserted into the surgical device multi-socket 1, 300, the user no longer risks to insert a plug into the wrong socket at the high-frequency generator and/or to unintendedly connect incompatible devices simultaneously to the high-frequency generator or to unintendedly operate incompatible devices simultaneously. Such a mix-up or inserting of the plug into a wrong socket, respectively, may cause damage to the device or the patient, especially during the surgery procedure so that the solution pursuant to the invention optimizes the safety during the surgery procedure.

Furthermore, the high number of compatible plugs has the result that only one surgical device multi-socket must be integrated into the high-frequency generator 50 and not, as previously, for each plug a socket specifically designed for the respective plug. In turn, this has the result that fewer space is required for the surgical device multi-socket so that a more compact design of the high-frequency generator can be realized. Furthermore, electro-surgical instruments from different manufacturers and with different plugs can be used at a single high-frequency generator so that, in a cost efficient manner, only one single high-frequency generator must be used which is able to serve a plurality of different electro-surgical instruments without this requiring the use of adapters.

FIG. 6 shows a surgical device multi-socket known in prior art for a Bovie plug. The surgical device multi-socket 120 comprises a first contact opening 124, a second contact opening 126 and a third contact opening 128. The second contact opening 126 is arranged adjacently to the first contact opening 124, and the third contact opening 128 is arranged adjacently to the second contact opening 126, wherein the first contact opening 124 is not arranged adjacently to the third contact opening 128. Furthermore, the contact openings 124, 126, 128 are arranged on a straight line in such a way that the centers of the contact openings 124, 126, 128 are arranged on the straight line. An arrangement of several plugs is not possible or only possible to a limited extent in the case of the surgical device multi-socket 120. Furthermore, the surgical device multi-socket 120 is not designed for the connection of coaxial plugs.

The surgical device multi-socket 120 further comprises a large contact opening 122 which has a diameter in orthogonal direction to the insertion direction which is twice as large as the diameter of the contact opening 124, 126, 128. Furthermore, in relation to the direction of the previously mentioned straight line, the large contact opening 122 is arranged between the second contact opening 126 and the third contact opening 128. Furthermore, it can be seen that the center of the large contact opening 122 is located at a distance from the straight line. In the installed state of the surgical device multi-socket 120, the center of the large contact opening 122 is arranged above the center of the contact opening 124, 126, 128. The large contact opening 122 is in particular designed for the connection of Bovie plugs.

The surgical device multi-socket 130 known in prior art and shown in FIG. 7 comprises essentially the same structure or arrangement, respectively, as the surgical device multi-socket 120 in FIG. 6. The surgical device multi-socket 130 comprises a first contact opening 134, a second contact opening 136 and a third contact opening 138, which are arranged analogously to the contact openings 124, 126, 128 of the surgical device multi-socket 120. Instead of the large contact opening 122 of the surgical device multi-socket 120, the surgical device multi-socket 130 shown in this figure has a coaxial socket 132. The center of the coaxial socket 132 is arranged essentially in the same location as the center of the large contact opening 122 at the surgical device multi-socket 120. In case of the surgical device multi-socket 130, as well, an arrangement of several plugs is not possible or only possible to a limited extent. Furthermore, the surgical device multi-socket 130 is not designed for the connection of Bovie plugs.

FIGS. 8a-8d show another exemplary embodiment of a surgical device multi-socket pursuant to the invention. The surgical device multi-socket 400 extends in the direction of a width B from a first end 402 to a second end 404.

Furthermore, the surgical device multi-socket 400 comprises a first contact opening 414, a second contact opening 416 and a third contact opening 418. Of said contact openings 414, 416, 418, the first contact opening 414 is the one which faces the first end. The third contact opening 418, on the other hand, is the contact opening which faces the second end 404. The second contact opening 416 is arranged in the direction of the width between the first contact opening 414 and the third contact opening 418.

The contact openings 414, 416, 418 respectively comprise the same diameter orthogonal to an insertion direction and furthermore a center. The centers of the contact openings 414, 416, 418 are located on a horizontal line 408, which is aligned in the direction of the width B. With regard to the width B it can be seen that the distance between the first contact opening 414 and the second contact opening 416 is clearly smaller than the distance between the second contact opening 416 and the third contact opening 418.

Furthermore, the surgical device multi-socket 400 comprises a coaxial socket 420 and a fourth contact opening 422. The fourth contact opening 422 has a diameter orthogonal to an insertion direction which is twice as large as the respective diameters of the contact openings 414, 416, 418.

The coaxial socket 420 and the fourth contact opening 422 respectively have a center, wherein the centers of the coaxial socket 420 and the fourth contact opening 422 are arranged on a vertical line 410, wherein said vertical line is arranged parallel to a height of the surgical device multi-socket. Furthermore, it can be seen that, in relation to the width B, the centers of the coaxial socket 420 and the fourth contact opening 422 are arranged between the second contact opening 416 and the third contact opening 418. In particular, the distance between the centers of the coaxial socket 420 and the fourth contact opening 422 and the center of the second contact opening 416 and the center of the third contact opening 418 is the same. In relation to the height, the center of the coaxial socket 420 is located below the horizontal line 408. The center of the fourth contact opening 422 is located above the horizontal line 408, in relation to the height.

FIGS. 9 to 11 show the use of the surgical device multi-socket 400, wherein respectively a state with different plugs 220, 230, 240 is shown. In FIG. 9, the first contact opening 414, the second contact opening 416 and the third contact opening 418 are used for accommodating a three-pin plug 220 with a first contact pin 221, a second contact pin 222 and a third contact pin 223. The three-pin plug 220 with the first contact pin 221, the second contact pin 222 and the third contact pin 223 is shown in a different perspective in FIG. 12.

FIG. 10 shows how a plug with a large contact pin, also known in prior art as Bovie pin, is arranged at the surgical device multi-socket 400. The plug with the large contact pin 230 is also once again shown in a different perspective in FIG. 13. FIG. 11 shows the use of a coaxial plug at the surgical device multi-socket 400, where the coaxial plug 240 is arranged in the coaxial socket 420. Such a coaxial plug is shown by way of example from a different perspective in FIG. 13.

Compared to the surgical device multi-sockets known in prior art, the surgical device multi-socket 400 has a plurality of advantages. The plug options of the currently used sockets at surgical devices are integrated into a single new socket in a previously unknown arrangement so that, all in all, a practicable, safe and cost efficient high-frequency generator can be provided by means of the surgical device multi-socket 400. The sockets may, for example, be arranged in such a way that two or more plugs can be arranged at the socket simultaneously. Thus, two or more plugs can be connected to the surgical device multi-socket 400. From this, it can be inferred that only one socket or, as the case may be, if need be, two sockets have to be arranged for a high-frequency generator so that the number of sockets is reduced. This leads to various advantages with regard to the manufacture of the sockets as such, and, therefore, to clearly lower costs for the manufacturer of high-frequency generators. Furthermore, as a result of the arrangement, the connection options are able to be arranged in a compact space so that, all in all, surface area at the high-frequency generator is saved and e.g. a particularly compact design of the generator is made possible. Since, in the medical environment, space in particular is expensive, this means a further cost reduction. The saved space at the high-frequency generator may e.g. also be used for the arrangement of other function elements, such as screens or operating elements. In addition, said arrangement makes it possible to prevent wrong plug connections. Consequently, the probability of mistakes during a surgical operation is reduced so that the safety of the use of an electro-surgical system is clearly increased by means of a surgical device multi-socket 400. Furthermore, advantages especially in the cost area are achieved through logistic advantages and larger purchase quantities.

REFERENCE NUMBERS 1, 300, 400 surgical device multi-socket
2 first end
3 second end
10 coaxial socket
11 inner sleeve
12 inner coaxial socket opening
13 outer sleeve
14 outer coaxial socket opening
16 coaxial socket connection end
20 first contact opening
22 first contact opening connection end
30 second contact opening
32 second contact opening connection end
40 positioning opening
42 positioning opening connection end
50 high-frequency generator
60a, 60b plug
61 first electro-surgical instrument
62 second electro-surgical instrument
63 third electro-surgical instrument
64 fourth electro-surgical instrument
65,65a connection cable
70 electro-surgical device plug
80 electro-surgical system
110 coaxial plug element
120 surgical device multi-socket
122 large contact opening
124 first contact opening
126 second contact opening
128 third contact opening
130 surgical device multi-socket
132 coaxial socket
134 first contact opening
136 second contact opening
138 third contact opening
210 contact pin
220 three-pin plug
221 first contact pin 222 second contact pin
223 third contact pin
230 plug with large contact pin
240 coaxial plug
402 first end
404 second end
408 horizontal line
410 vertical line
414 first contact opening
416 second contact opening
418 third contact opening
420 coaxial socket
422 fourth contact opening
B width
H height

The invention claimed is:

1. A surgical device multi-socket for a high-frequency generator for connecting a bipolar applicator, the surgical device multi-socket comprising:
a coaxial socket that includes an inner sleeve and an outer sleeve arranged concentrically about a same axis, the coaxial socket being configured to receive a coaxial plug element that includes an inner contact pin and an outer contact ring;
a first contact opening configured to receive a contact pin, the first contact opening being spaced apart from the coaxial socket; and
a positioning opening designed to accommodate a positioning pin, wherein:
the coaxial socket, the first contact opening and a second contact opening are arranged such that a straight line connects centers of the coaxial socket, the first contact opening and the second contact opening; and
a center of the positioning opening is arranged at a distance from a straight line connecting the centers of the coaxial socket, the first contact opening and a second contact opening such that the positioning opening is not aligned with the straight line and the positioning opening is provided off-center and between one of the first contact opening and the second contact opening and the coaxial socket.

2. A surgical device multi-socket pursuant to claim 1, wherein the first contact opening is adjacent to a second contact opening.

3. A surgical device multi-socket pursuant to claim 1, wherein:
a distance between a central axis of the first contact opening and a central axis of a second contact opening is smaller than at least one of: a distance between the central axis of the first contact opening and a central axis of the coaxial socket, a distance between the central axis of the second contact opening and a central axis of the coaxial socket, or a distance between a central axis of a positioning opening and the central axis of the coaxial socket,
the distance between the central axis of the first contact opening and the central axis of the coaxial socket is larger than the distance between the central axis of the second contact opening and the central axis of the coaxial socket; and
the distance between the central axis of the second contact opening and the central axis of the coaxial socket is larger than the distance between the central axis of the positioning opening and the central axis of the coaxial socket.

4. A surgical device multi-socket pursuant to claim 1, wherein:
a distance between a central axis of the first contact opening and a central axis of a second contact opening is a maximum of 5 times a diameter of one of the first contact opening and the second contact opening.

5. A surgical device multi-socket pursuant to claim 1, wherein:
the coaxial socket comprises at least one of:
a coaxial connection end configured to receive a coaxial plug element; or
a first contact connection end configured to receive a contact pin;
a second contact opening comprises a second contact connection end configured to receive a second contact pin; and
a positioning opening comprises a positioning connection end configured to receive a positioning pin; and
at least two connection ends are located along a same plane.

6. An electro-surgical high-frequency generator, comprising
a surgical device multi-socket according to claim 1.

7. An electro-surgical system, comprising:
a high-frequency generator pursuant to claim 6, and
an electro-surgical instrument that is or can be connected via the surgical device multi-socket of the high-frequency generator.

8. A surgical device multi-socket pursuant to claim 1, wherein:
a central axis of the coaxial socket is 28-29 mm from a central axis of the first contact opening.

9. A surgical device multi-socket pursuant to claim 1, wherein:
a central axis of the coaxial socket is 21-23 mm from a central axis of the second contact opening.

10. A surgical device multi-socket for a high-frequency generator for connecting a monopolar applicator, the surgical device multi-socket comprising a coaxial socket that includes an inner sleeve and an outer sleeve arranged concentrically about a same axis, the coaxial socket being configured to receive a coaxial plug element that includes an inner contact pin and an outer contact ring; and
a first contact opening configured to receive a contact pin of a three-pin plug, the first contact opening being spaced apart from the coaxial socket
a second contact opening which is designed to accommodate a contact pin, and
a third contact opening which is designed to accommodate a contact pin, wherein centers of the first contact opening and the second contact opening and the third contact opening are arranged on a straight line, and
a fourth contact opening, which is designed to accommodate a Bovie plug, wherein:
the coaxial socket and a fourth contact opening are arranged between the second contact opening and the third contact opening, and
the coaxial socket and the fourth contact opening are arranged such that a first line connecting a center of the coaxial socket and a center of the fourth contact opening is orthogonal to a second line connecting a center of the first contact opening, a center of the second contact opening, and a center of the third contact opening.

11. A surgical multi-socket pursuant to claim 10, wherein the fourth contact opening and one, two or several further contact openings respectively have a diameter arranged in orthogonal direction to an insertion direction,
- wherein the one, two or several further contact openings are chosen from the group consisting of the first contact opening, the second contact opening, and the third contact opening,
- wherein the diameter of the fourth contact opening is larger than the diameter or, respectively, the diameters of the one, two or several further contact openings,
- wherein the diameter of the fourth contact opening is between 6 mm and 10 mm.

12. An electro-surgical high-frequency generator, comprising a surgical device multi-socket according to claim 9.

13. An electro-surgical system, comprising:
- a high-frequency generator pursuant to claim 12, and
- an electro-surgical instrument that is or can be connected via the surgical device multi-socket of the high-frequency generator.

14. A surgical device multi-socket pursuant to claim 9,
- the first contact opening is arranged on a side of the second contact opening that faces away from the third contact opening.

15. A surgical device multi-socket pursuant to claim 14, wherein:
- the coaxial socket and the fourth contact opening have enough distance between them to simultaneously arrange a coaxial plug in the coaxial socket and a contact pin in the fourth contact opening.

* * * * *